United States Patent
Zhang et al.

(10) Patent No.: US 12,383,747 B2
(45) Date of Patent: Aug. 12, 2025

(54) SUPRAVENTRICULAR TACHYARRHYTHMIA DISCRIMINATION

(71) Applicant: Medtronic, Inc., Minneapolis, MN (US)

(72) Inventors: Xusheng Zhang, Shoreview, MN (US); Jian Cao, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 18/739,312

(22) Filed: Jun. 10, 2024

(65) Prior Publication Data

US 2024/0325762 A1    Oct. 3, 2024

Related U.S. Application Data

(63) Continuation of application No. 17/407,534, filed on Aug. 20, 2021, now Pat. No. 12,011,598, which is a
(Continued)

(51) Int. Cl.
| | |
|---|---|
| A61N 1/36 | (2006.01) |
| A61B 5/352 | (2021.01) |
| A61B 5/363 | (2021.01) |
| A61N 1/362 | (2006.01) |
| A61N 1/365 | (2006.01) |

(Continued)

(52) U.S. Cl.
CPC ............ *A61N 1/3621* (2013.01); *A61B 5/352* (2021.01); *A61B 5/363* (2021.01); *A61N 1/3624* (2013.01); *A61N 1/36592* (2013.01); *A61N 1/3704* (2013.01); *A61N 1/39622* (2017.08)

(58) Field of Classification Search
CPC ... A61N 1/3621; A61N 1/3956; A61N 1/0464
See application file for complete search history.

(56) References Cited

U.S. PATENT DOCUMENTS

| | | |
|---|---|---|
| 5,240,009 A | 8/1993 | Williams |
| 5,354,316 A | 10/1994 | Keimel |
| (Continued) | | |

FOREIGN PATENT DOCUMENTS

| | | |
|---|---|---|
| EP | 2014228 A1 | 1/2009 |

OTHER PUBLICATIONS (PCT/US2018/065131) PCT Notification of Transmittal of the International Search Report and the Written Opinion of the International Searching Authority, Mailed Mar. 27, 2019, 15 pages.
(Continued)

*Primary Examiner* — Michael J D'Abreu

(57) ABSTRACT

Techniques are described for discriminating SVT and, in particular, rapidly conducting AF. The techniques include detecting an onset of a fast rate of ventricular events sensed from a cardiac electrical signal and detecting a pause in the fast rate of ventricular sensed events. A threshold number of ventricular event intervals required to detect a ventricular tachyarrhythmia is detected with each of the threshold number of ventricular event intervals being less than a tachyarrhythmia detection interval. Detection of the ventricular tachyarrhythmia and an electrical stimulation therapy for treating the ventricular tachyarrhythmia are withheld in response to at least the pause being detected.

21 Claims, 10 Drawing Sheets

Related U.S. Application Data continuation of application No. 16/217,207, filed on Dec. 12, 2018, now Pat. No. 11,116,981.

(60) Provisional application No. 62/599,071, filed on Dec. 15, 2017.

(51) Int. Cl.
*A61N 1/37* (2006.01)
*A61N 1/39* (2006.01)

(56) References Cited

U.S. PATENT DOCUMENTS

| | | | |
|---|---|---|---|
| 5,545,186 A | 8/1996 | Olson | |
| 5,730,142 A | 3/1998 | Sun et al. | |
| 5,893,882 A | 4/1999 | Peterson | |
| 6,212,428 B1 | 4/2001 | Hsu | |
| 6,393,316 B1 | 5/2002 | Gillberg | |
| 7,031,770 B2 | 4/2006 | Collins et al. | |
| 7,031,771 B2 | 4/2006 | Brown | |
| 7,076,289 B2 | 7/2006 | Sarkar | |
| 7,158,827 B2 | 1/2007 | Corbucci | |
| 7,729,763 B2 | 6/2010 | Kornet | |
| 7,761,150 B2 | 7/2010 | Ghanem | |
| 7,894,883 B2 | 2/2011 | Gunderson et al. | |
| 8,073,536 B2 | 12/2011 | Gunderson et al. | |
| 8,073,537 B2 | 12/2011 | Gunderson et al. | |
| 8,160,684 B2 | 4/2012 | Ghanem | |
| 8,165,675 B2 | 4/2012 | Wang | |
| 8,271,073 B2 | 9/2012 | Zhang et al. | |
| 8,271,081 B2 | 9/2012 | Hauck | |
| 8,301,235 B2 | 10/2012 | Zhang et al. | |
| 8,332,022 B2 | 12/2012 | Brown | |
| 8,401,644 B2 | 3/2013 | Gunderson et al. | |
| 8,406,872 B2 | 3/2013 | Stadler et al. | |
| 8,437,842 B2 | 5/2013 | Zhang | |
| 8,532,772 B2 | 9/2013 | Gunderson et al. | |
| 8,543,198 B2 | 9/2013 | Zhang et al. | |
| 8,750,976 B2 | 6/2014 | Stadler et al. | |
| 8,768,459 B2 | 7/2014 | Ghosh et al. | |
| 8,831,725 B2 | 9/2014 | Gunderson et al. | |
| 8,849,400 B2 | 9/2014 | Gunderson et al. | |
| 8,983,585 B2 | 3/2015 | Zhang et al. | |
| 9,682,238 B2 | 6/2017 | Zhang et al. | |
| 2007/0135848 A1 | 6/2007 | Kim et al. | |
| 2008/0281368 A1 | 11/2008 | Bulkes et al. | |
| 2009/0270936 A1 | 10/2009 | Benser | |
| 2009/0299205 A1 | 12/2009 | Chow | |
| 2010/0036447 A1 | 2/2010 | Zhang et al. | |
| 2013/0096446 A1 | 4/2013 | Michael et al. | |
| 2015/0306375 A1 | 10/2015 | Marshall | |
| 2015/0306410 A1 | 10/2015 | Marshall | |
| 2016/0158567 A1 | 6/2016 | Marshall | |
| 2016/0175603 A1 | 6/2016 | Sheldon et al. | |
| 2017/0043173 A1 | 2/2017 | Sharma et al. | |
| 2017/0281034 A1 | 10/2017 | Higgins et al. | |
| 2017/0312532 A1 | 11/2017 | Zhang et al. | |
| 2017/0312533 A1 | 11/2017 | Grinberg et al. | |
| 2017/0312534 A1 | 11/2017 | Cao et al. | |
| 2017/0354827 A1 | 12/2017 | Zhang et al. | |
| 2018/0028085 A1 | 2/2018 | Zhang et al. | |
| 2018/0028087 A1 | 2/2018 | Zhang et al. | |
| 2018/0303368 A1 | 10/2018 | Zhang et al. | |

OTHER PUBLICATIONS

Yijiao Qian, "Electrophysiologic Characteristics of Tachyarrhythmias in Children and the Efficacy of Radiofrequency Ablation Analysis", Shanghai Jiao Tong University, Feb. 15, 2017, 92 pages.
Whinnett, et al. "Diagnosis and Management of Supraventricular Tachycardia", BMJ, Dec. 31, 2012, 9 pages.
"Office Action Issued in Chinese Patent Application No. 201880080538.4", Mailed Date: Jan. 16, 2024, 15 Pages.

SUPRAVENTRICULAR TACHYARRHYTHMIA DISCRIMINATION

CROSS REFERENCE TO RELATED APPLICATIONS

This application is a continuation of U.S. patent application Ser. No. 17/407,534, filed Aug. 20, 2021, which is a continuation of U.S. patent application Ser. No. 16/217,207, filed on Dec. 12, 2018, granted as U.S. Pat. No. 11,116,981, which claims the benefit of the filing date of provisional U.S. Patent Application No. 62/599,071, filed Dec. 15, 2017, all of which are incorporated herein by reference in their entirety.

TECHNICAL FIELD

The disclosure relates generally to a medical device system and method for discriminating supraventricular tachyarrhythmia, particularly rapidly conductive atrial fibrillation, from ventricular tachyarrhythmia.

BACKGROUND

Medical devices, such as cardiac pacemakers and implantable cardioverter defibrillators (ICDs), provide therapeutic electrical stimulation to a heart of a patient via electrodes carried by one or more medical electrical leads and/or electrodes on a housing of the medical device. The electrical stimulation may include signals such as pacing pulses or cardioversion or defibrillation shocks. In some cases, a medical device may sense cardiac electrical signals attendant to the intrinsic or pacing-evoked depolarizations of the heart and control delivery of stimulation signals to the heart based on sensed cardiac electrical signals.

Upon detection of an abnormal rhythm, such as bradycardia, tachycardia or fibrillation, an appropriate electrical stimulation signal or signals may be delivered to restore or maintain a more normal rhythm of the heart. For example, an ICD may deliver pacing pulses to the heart of the patient upon detecting bradycardia or tachycardia or deliver cardioversion or defibrillation shocks to the heart upon detecting tachycardia or fibrillation. The ICD may sense the cardiac electrical signals in a heart chamber and deliver electrical stimulation therapies to the heart chamber using electrodes carried by transvenous medical electrical leads. Cardiac signals sensed within the heart generally have a high signal strength and quality for reliably sensing cardiac electrical events, such as R-waves associated with ventricular events. In other examples, a non-transvenous lead may be coupled to the ICD, in which case cardiac signal sensing presents new challenges in accurately sensing cardiac electrical events and properly detecting and discriminating between different types of cardiac arrhythmias.

Proper detection and discrimination of different tachyarrhythmias is important in automatically selecting and delivering an effective electrical stimulation therapy by an implantable medical device system and avoiding unnecessary therapies. For example, a supraventricular tachyarrhythmia originates in the upper, atrial heart chambers and is conducted to the lower, ventricular heart chambers. A supraventricular tachyarrhythmia (SVT) is generally not successfully terminated by delivering electrical stimulation therapy to the ventricles because the heart rhythm is arising from the upper heart chambers. A ventricular tachyarrhythmia that originates in the lower, ventricular heart chambers, on the other hand, generally can be successfully treated by delivering electrical stimulation therapies to the ventricles to terminate the abnormal ventricular rhythm. Accordingly, discrimination of supraventricular tachyarrhythmia that originates in the upper heart chambers from ventricular tachyarrhythmia that originates in the lower heart chambers allows for appropriate therapy selection and delivery while avoiding unnecessary or potentially ineffective electrical stimulation therapy from being delivered to the patient's heart.

SUMMARY

In general, the disclosure is directed to techniques for discriminating SVT from ventricular tachyarrhythmias, e.g., ventricular tachycardia (VT) and ventricular fibrillation (VF), and withholding VT and VF detection and therapies when SVT is detected. In some examples, a medical device system, such as an ICD system, operating according to the techniques disclosed herein may detect rapidly conducted atrial fibrillation (AF) by detecting a pause in the rate of sensed ventricular events. The pause in the rate of sensed ventricular events may be detected based on at least one relatively long interval between consecutively sensed R-waves and morphology features of a cardiac electrical signal. If a pause in a fast ventricular rate is detected and other VT or VF detection criteria are satisfied, the VT or VF detection and therapy may be delayed or withheld.

In one example, the disclosure provides a device comprising a therapy delivery circuit configured to generate an electrical stimulation therapy, a sensing circuit configured to receive a first cardiac electrical signal via a first sensing electrode vector and sense ventricular events from the first cardiac electrical signal, and a control circuit coupled to the sensing circuit and the therapy delivery circuit. The control circuit is configured to determine that a first plurality of the sensed ventricular events meet a fast ventricular rate criteria; subsequent to determining the fast ventricular rate criteria is met, detect a pause in a rate of a second plurality of the sensed ventricular events; detect from the first cardiac electrical signal a threshold number of ventricular event intervals required to detect a ventricular tachyarrhythmia, each of the threshold number of ventricular event intervals being less than a tachyarrhythmia detection interval; and withhold the electrical stimulation therapy for treating the ventricular tachyarrhythmia in response to at least the pause being detected.

In another example, the disclosure provides a method comprising receiving a first cardiac electrical signal; sensing ventricular events from the first cardiac electrical signal; determining that a first plurality of the sensed ventricular events meet a fast ventricular rate criteria; subsequent to determining the fast ventricular rate criteria is met, detecting a pause in a rate of a second plurality of the sensed ventricular events; detecting from the first cardiac electrical signal a threshold number of ventricular event intervals required to detect a ventricular tachyarrhythmia, each of the threshold number of ventricular event intervals being less than a tachyarrhythmia detection interval; and withholding an electrical stimulation therapy for treating the ventricular tachyarrhythmia in response to at least the pause being detected.

In another example, the disclosure provides a non-transitory, computer-readable storage medium comprising a set of instructions which, when executed by a processor, cause the processor to receive a first cardiac electrical signal; sense ventricular events from the first cardiac electrical signal; determine that a first plurality of the sensed ventricular events meet a fast ventricular rate criteria; subsequent to determining the fast ventricular rate criteria is met, detect a pause in a rate of a second plurality of the sensed ventricular events; detect from the first cardiac electrical signal a threshold number of ventricular event intervals required to detect a ventricular tachyarrhythmia, each of the threshold number of ventricular event intervals being less than a tachyarrhythmia detection interval; and withhold an electrical stimulation therapy for treating the ventricular tachyarrhythmia in response to at least the pause being detected.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

DETAILED DESCRIPTION

In general, this disclosure describes techniques for discriminating SVT from VT and VF by a cardiac medical device or system and withholding detection of a ventricular tachyarrhythmia or therapy to treat the ventricular tachyarrhythmia in response to detecting SVT. Criteria for detecting ventricular tachyarrhythmia, such as heart rate-based criteria, may become satisfied in the presence of SVT. As such, heart rate alone may be insufficient for reliably discriminating between SVT and VT/VF. Techniques for detecting SVT as described herein allow a tachyarrhythmia detection and/or therapy to be withheld or delayed when evidence of SVT is identified.

In some examples, the cardiac medical device system may be an extra-cardiovascular ICD system. As used herein, the term "extra-cardiovascular" refers to a position outside the blood vessels, heart, and pericardium surrounding the heart of a patient. Implantable electrodes carried by extra-cardiovascular leads may be positioned extra-thoracically (outside the ribcage and sternum) or intra-thoracically (beneath the ribcage or sternum) but generally not in intimate contact with myocardial tissue. The techniques disclosed herein for detecting SVT and withholding a VT/VF detection may be applied to a cardiac electrical signal acquired using extra-cardiovascular electrodes.

These techniques are presented herein in conjunction with an ICD and implantable medical lead carrying extra-cardiovascular electrodes, but aspects of the techniques may be utilized in conjunction with other cardiac medical devices or systems. For example, the techniques for detecting SVT, such as rapidly conductive atrial fibrillation, as described in conjunction with the accompanying drawings may be implemented in any implantable or external medical device enabled for sensing cardiac electrical signals, including implantable pacemakers, ICDs or cardiac monitors coupled to transvenous, pericardial or epicardial leads carrying sensing and therapy delivery electrodes; leadless pacemakers, ICDs or cardiac monitors having housing-based sensing electrodes; and external or wearable pacemakers, defibrillators, or cardiac monitors coupled to external, surface or skin electrodes.

Figure 1A:
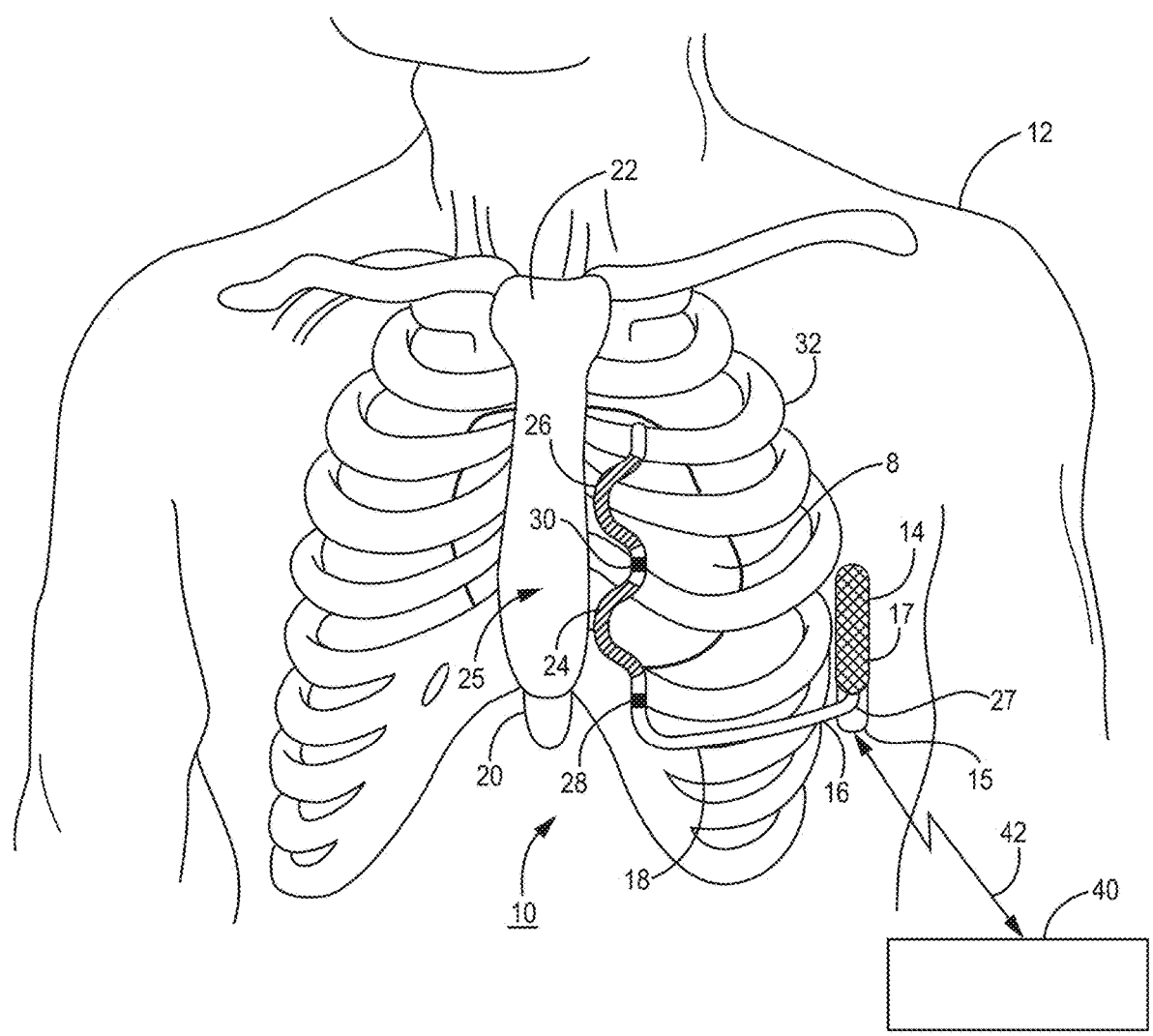
FIGS. 1A and 1B are conceptual diagrams of an extra-cardiovascular ICD system according to one example.
Figure 1B:
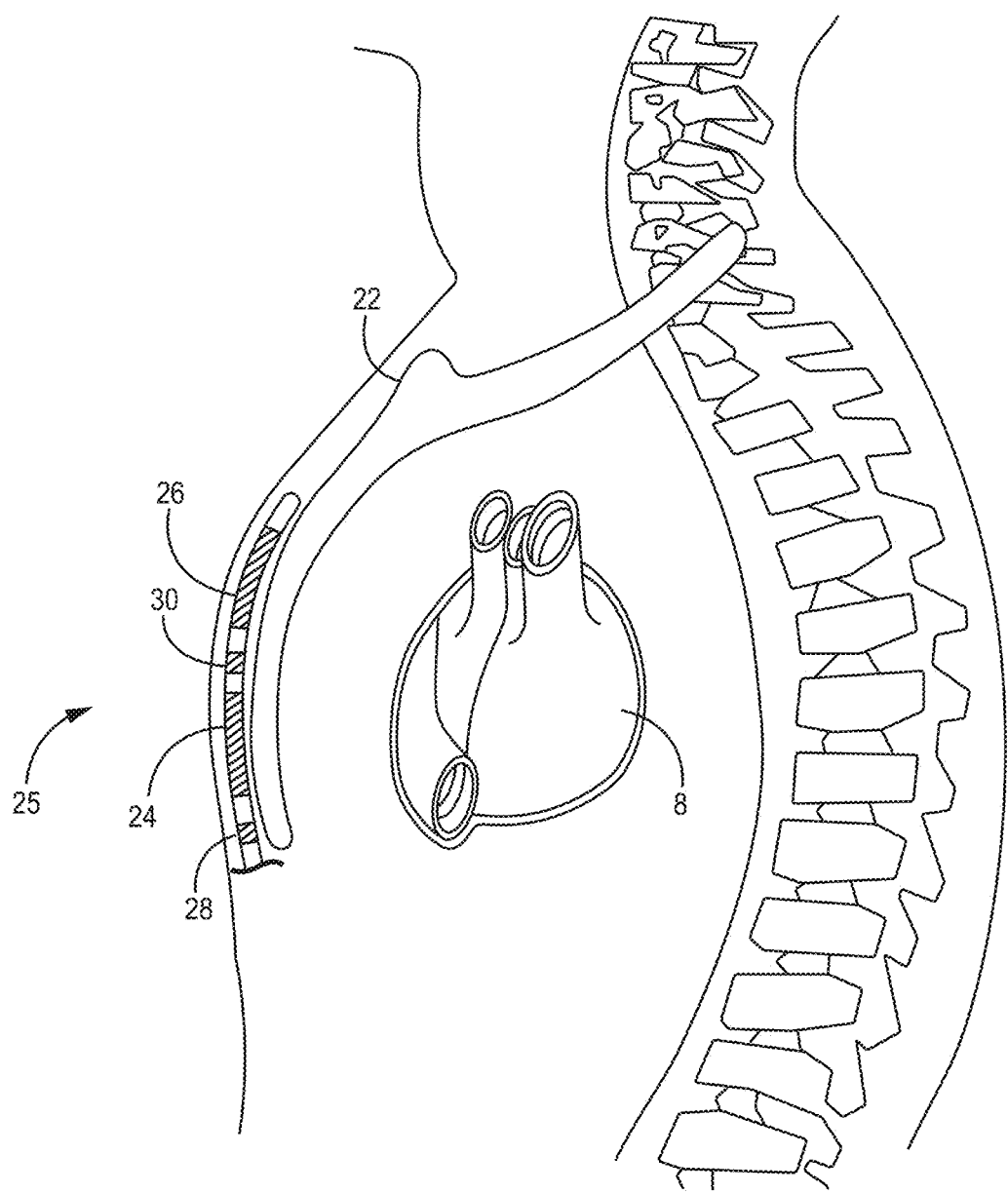

FIGS. 1A and 1B are conceptual diagrams of an extra-cardiovascular ICD system 10 according to one example. FIG. 1A is a front view of ICD system 10 implanted within patient 12. FIG. 1B is a side view of ICD system 10 implanted within patient 12. ICD system 10 includes an ICD 14 connected to an extra-cardiovascular electrical stimulation and sensing lead 16. FIGS. 1A and 1B are described in the context of an ICD system 10 capable of providing defibrillation and/or cardioversion shocks and pacing pulses.

ICD 14 includes a housing 15 that forms a hermetic seal that protects internal components of ICD 14. The housing 15 of ICD 14 may be formed of a conductive material, such as titanium or titanium alloy. The housing 15 may function as an electrode (sometimes referred to as a "can" electrode). Housing 15 may be used as an active can electrode for use in delivering cardioversion/defibrillation (CV/DF) shocks or other high voltage pulses delivered using a high voltage therapy circuit. In other examples, housing 15 may be available for use in delivering unipolar, low voltage cardiac pacing pulses and/or for sensing cardiac electrical signals in combination with electrodes carried by lead 16. In other instances, the housing 15 of ICD 14 may include a plurality of electrodes on an outer portion of the housing. The outer portion(s) of the housing 15 functioning as an electrode(s) may be coated with a material, such as titanium nitride, e.g., for reducing post-stimulation polarization artifact.

ICD 14 includes a connector assembly 17 (also referred to as a connector block or header) that includes electrical feedthroughs crossing housing 15 to provide electrical connections between conductors extending within the lead body 18 of lead 16 and electronic components included within the housing 15 of ICD 14. As will be described in further detail herein, housing 15 may house one or more processors, memories, transceivers, electrical cardiac signal sensing circuitry, therapy delivery circuitry, power sources and other components for sensing cardiac electrical signals, detecting a heart rhythm, and controlling and delivering electrical stimulation pulses to treat an abnormal heart rhythm.

Elongated lead body 18 has a proximal end 27 that includes a lead connector (not shown) configured to be connected to ICD connector assembly 17 and a distal portion 25 that includes one or more electrodes. In the example illustrated in FIGS. 1A and 1B, the distal portion 25 of lead body 18 includes defibrillation electrodes 24 and 26 and pace/sense electrodes 28 and 30. In some cases, defibrillation electrodes 24 and 26 may together form a defibrillation electrode in that they may be configured to be activated concurrently. Alternatively, defibrillation electrodes 24 and 26 may form separate defibrillation electrodes in which case each of the electrodes 24 and 26 may be activated independently.

Electrodes 24 and 26 (and in some examples housing 15) are referred to herein as defibrillation electrodes because they are utilized, individually or collectively, for delivering high voltage stimulation therapy (e.g., cardioversion or defibrillation shocks). Electrodes 24 and 26 may be elongated coil electrodes and generally have a relatively high surface area for delivering high voltage electrical stimulation pulses compared to pacing and sensing electrodes 28 and 30. However, electrodes 24 and 26 and housing 15 may also be utilized to provide pacing functionality, sensing functionality or both pacing and sensing functionality in addition to or instead of high voltage stimulation therapy. In this sense, the use of the term "defibrillation electrode" herein should not be considered as limiting the electrodes 24 and 26 for use in only high voltage cardioversion/defibrillation shock therapy applications. For example, electrodes 24 and 26 may be used in a sensing vector used to sense cardiac electrical signals and detect and discriminate SVT, VT and VF.

Electrodes 28 and 30 are relatively smaller surface area electrodes which are available for use in sensing electrode vectors for sensing cardiac electrical signals and may be used for delivering relatively low voltage pacing pulses in some configurations. Electrodes 28 and 30 are referred to as pace/sense electrodes because they are generally configured for use in low voltage applications, e.g., used as either a cathode or anode for delivery of pacing pulses and/or sensing of cardiac electrical signals, as opposed to delivering high voltage cardioversion defibrillation shocks. In some instances, electrodes 28 and 30 may provide only pacing functionality, only sensing functionality or both.

ICD 14 may obtain cardiac electrical signals corresponding to electrical activity of heart 8 via a combination of sensing vectors that include combinations of electrodes 24, 26, 28 and/or 30. In some examples, housing 15 of ICD 14 is used in combination with one or more of electrodes 24, 26, 28 and/or 30 in a sensing electrode vector. Various sensing electrode vectors utilizing combinations of electrodes 24, 26, 28, and 30 and housing 15 are described below for acquiring first and second cardiac electrical signals using respective first and/or second sensing electrode vectors that may be selected by sensing circuitry included in ICD 14.

In the example illustrated in FIGS. 1A and 1B, electrode 28 is located proximal to defibrillation electrode 24, and electrode 30 is located between defibrillation electrodes 24 and 26. One, two or more pace/sense electrodes may be carried by lead body 18. For instance, a third pace/sense electrode may be located distal to defibrillation electrode 26 in some examples. Electrodes 28 and 30 are illustrated as ring electrodes; however, electrodes 28 and 30 may comprise any of a number of different types of electrodes, including ring electrodes, short coil electrodes, hemispherical electrodes, directional electrodes, segmented electrodes, or the like. Electrodes 28 and 30 may be positioned at any location along lead body 18 and are not limited to the positions shown. In other examples, lead 16 may include none, one or more pace/sense electrodes and/or one or more defibrillation electrodes.

In the example shown, lead 16 extends subcutaneously or submuscularly over the ribcage 32 medially from the connector assembly 27 of ICD 14 toward a center of the torso of patient 12, e.g., toward xiphoid process 20 of patient 12. At a location near xiphoid process 20, lead 16 bends or turns and extends superior subcutaneously or submuscularly over the ribcage and/or sternum, substantially parallel to sternum 22. Although illustrated in FIG. 1A as being offset laterally from and extending substantially parallel to sternum 22, the distal portion 25 of lead 16 may be implanted at other locations, such as over sternum 22, offset to the right or left of sternum 22, angled laterally from sternum 22 toward the left or the right, or the like. Alternatively, lead 16 may be placed along other subcutaneous or submuscular paths. The path of extra-cardiovascular lead 16 may depend on the location of ICD 14, the arrangement and position of electrodes carried by the lead body 18, and/or other factors.

Electrical conductors (not illustrated) extend through one or more lumens of the elongated lead body 18 of lead 16 from the lead connector at the proximal lead end 27 to electrodes 24, 26, 28, and 30 located along the distal portion 25 of the lead body 18. The elongated electrical conductors contained within the lead body 18 are each electrically coupled with respective defibrillation electrodes 24 and 26 and pace/sense electrodes 28 and 30, which may be separate respective insulated conductors within the lead body 18. The respective conductors electrically couple the electrodes 24, 26, 28, and 30 to circuitry, such as a therapy delivery circuit and/or a sensing circuit, of ICD 14 via connections in the connector assembly 17, including associated electrical feedthroughs crossing housing 15. The electrical conductors transmit therapy from a therapy delivery circuit within ICD 14 to one or more of defibrillation electrodes 24 and 26 and/or pace/sense electrodes 28 and 30 and transmit sensed electrical signals from one or more of defibrillation electrodes 24 and 26 and/or pace/sense electrodes 28 and 30 to the sensing circuit within ICD 14.

The lead body 18 of lead 16 may be formed from a non-conductive material, including silicone, polyurethane, fluoropolymers, mixtures thereof, and other appropriate materials, and shaped to form one or more lumens within which the one or more conductors extend. Lead body 18 may be tubular or cylindrical in shape. In other examples, the distal portion 25 (or all of) the elongated lead body 18 may have a flat, ribbon or paddle shape. Lead body 18 may be formed having a preformed distal portion 25 that is generally straight, curving, bending, serpentine, undulating or zig-zagging.

In the example shown, lead body 18 includes a curving distal portion 25 having two "C" shaped curves, which together may resemble the Greek letter epsilon, "ϵ." Defibrillation electrodes 24 and 26 are each carried by one of the two respective C-shaped portions of the lead body distal portion 25. The two C-shaped curves are seen to extend or curve in the same direction away from a central axis of lead body 18, along which pace/sense electrodes 28 and 30 are positioned. Pace/sense electrodes 28 and 30 may, in some instances, be approximately aligned with the central axis of the straight, proximal portion of lead body 18 such that mid-points of defibrillation electrodes 24 and 26 are laterally offset from pace/sense electrodes 28 and 30.

Other examples of extra-cardiovascular leads including one or more defibrillation electrodes and one or more pacing and sensing electrodes carried by curving, serpentine, undulating or zig-zagging distal portion of the lead body 18 that may be implemented with the techniques described herein are generally disclosed in pending U.S. Pat. Publication No. 2016/0158567 (Marshall, et al.), incorporated herein by reference in its entirety. The techniques disclosed herein are not limited to any particular lead body design, however. In other examples, lead body 18 is a flexible elongated lead body without any pre-formed shape, bends or curves. Various example configurations of extra-cardiovascular leads and electrodes and dimensions that may be implemented in conjunction with the SVT discrimination techniques disclosed herein are described in pending U.S. Publication No. 2015/0306375 (Marshall, et al.) and pending U.S. Publication No. 2015/0306410 (Marshall, et al.), both of which are incorporated herein by reference in their entirety.

ICD 14 analyzes the cardiac electrical signals received from one or more sensing electrode vectors to monitor for abnormal rhythms, such as bradycardia, SVT, VT or VF. ICD 14 may analyze the heart rate and morphology of the cardiac electrical signals to monitor for tachyarrhythmia in accordance with any of a number of tachyarrhythmia detection techniques. One example technique for detecting tachyarrhythmia is described in U.S. Pat. No. 7,761,150 (Ghanem, et al.), incorporated herein by reference in its entirety. Example techniques for detecting VT and VF are described below in conjunction with the accompanying figures. The techniques for discriminating SVT from VT or VF for withholding a VT or VF detection as disclosed herein may be incorporated in a variety of VT/VF detection algorithms. Examples of devices and tachyarrhythmia detection algorithms that may be adapted to utilize techniques for SVT discrimination described herein are generally disclosed in U.S. Pat. No. 5,354,316 (Keimel); U.S. Pat. No. 5,545,186 (Olson, et al.); U.S. Pat. No. 6,393,316 (Gillberg et al.); U.S. Pat. No. 7,031,771 (Brown, et al.); U.S. Pat. No. 8,160,684 (Ghanem, et al.), and U.S. Pat. No. 8,437,842 (Zhang, et al.), all of which patents are incorporated herein by reference in their entirety.

ICD 14 generates and delivers electrical stimulation therapy in response to detecting a tachyarrhythmia (e.g., VT or VF) using a therapy delivery electrode vector which may be selected from any of the available electrodes 24, 26, 28 30 and/or housing 15. ICD 14 may deliver ATP in response to VT detection, and in some cases may deliver ATP prior to a CV/DF shock or during high voltage capacitor charging in an attempt to avert the need for delivering a CV/DF shock. If ATP does not successfully terminate VT or when VF is detected, ICD 14 may deliver one or more CV/DF shocks via one or both of defibrillation electrodes 24 and 26 and/or housing 15. ICD 14 may deliver the CV/DF shocks using electrodes 24 and 26 individually or together as a cathode (or anode) and with the housing 15 as an anode (or cathode). ICD 14 may generate and deliver other types of electrical stimulation pulses such as post-shock pacing pulses or bradycardia pacing pulses using a pacing electrode vector that includes one or more of the electrodes 24, 26, 28, and 30 and the housing 15 of ICD 14.

FIGS. 1A and 1B are illustrative in nature and should not be considered limiting of the practice of the techniques disclosed herein. ICD 14 is shown implanted subcutaneously on the left side of patient 12 along the ribcage 32. ICD 14 may, in some instances, be implanted between the left posterior axillary line and the left anterior axillary line of patient 12. ICD 14 may, however, be implanted at other subcutaneous or submuscular locations in patient 12. For example, ICD 14 may be implanted in a subcutaneous pocket in the pectoral region. In this case, lead 16 may extend subcutaneously or submuscularly from ICD 14 toward the manubrium of sternum 22 and bend or turn and extend inferiorly from the manubrium to the desired location subcutaneously or submuscularly. In yet another example, ICD 14 may be placed abdominally. Lead 16 may be implanted in other extra-cardiovascular locations as well. For instance, as described with respect to FIGS. 2A-2C, the distal portion 25 of lead 16 may be implanted underneath the sternum/ribcage in the substernal space.

An external device 40 is shown in telemetric communication with ICD 14 by a communication link 42. External device 40 may include a processor, display, user interface, telemetry unit and other components for communicating with ICD 14 for transmitting and receiving data via communication link 42. Communication link 42 may be established between ICD 14 and external device 40 using a radio frequency (RF) link such as BLUETOOTH® communication, Wi-Fi, or Medical Implant Communication Service (MICS) or other RF or communication frequency bandwidth.

External device 40 may be embodied as a programmer used in a hospital, clinic or physician's office to retrieve data from ICD 14 and to program operating parameters and algorithms in ICD 14 for controlling ICD functions. External device 40 may be used to program cardiac event sensing parameters (e.g., R-wave sensing parameters), cardiac rhythm detection parameters (e.g., VT and VF detection parameters and SVT discrimination parameters) and therapy control parameters used by ICD 14. Data stored or acquired by ICD 14, including physiological signals or associated data derived therefrom, results of device diagnostics, and histories of detected rhythm episodes and delivered therapies, may be retrieved from ICD 14 by external device 40 following an interrogation command. External device 40 may alternatively be embodied as a home monitor or hand held device.

Figure 2A:
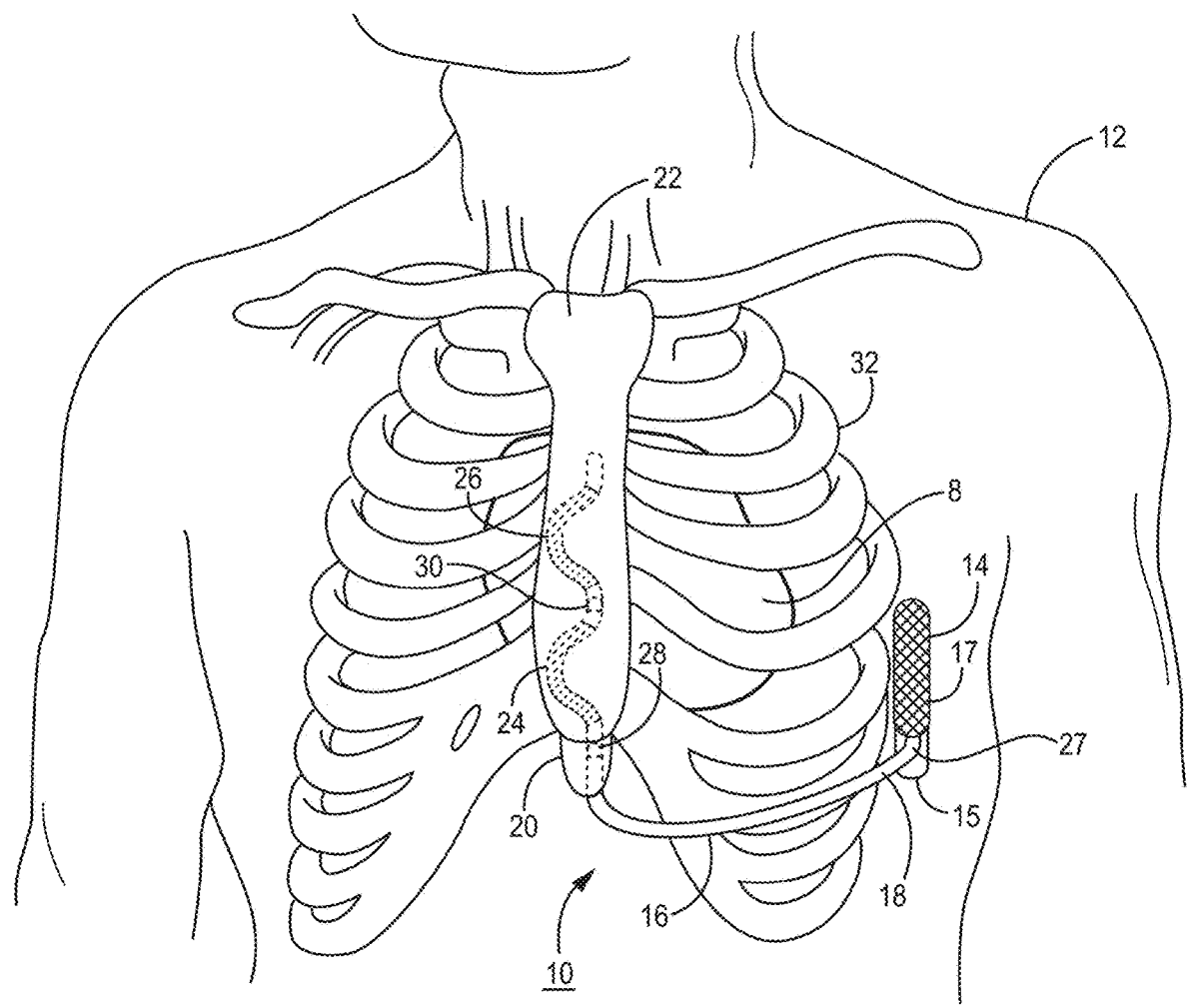
FIGS. 2A-2C are conceptual diagrams of a patient implanted with the extra-cardiovascular ICD system of FIG. 1A in a different implant configuration.
Figure 2B:
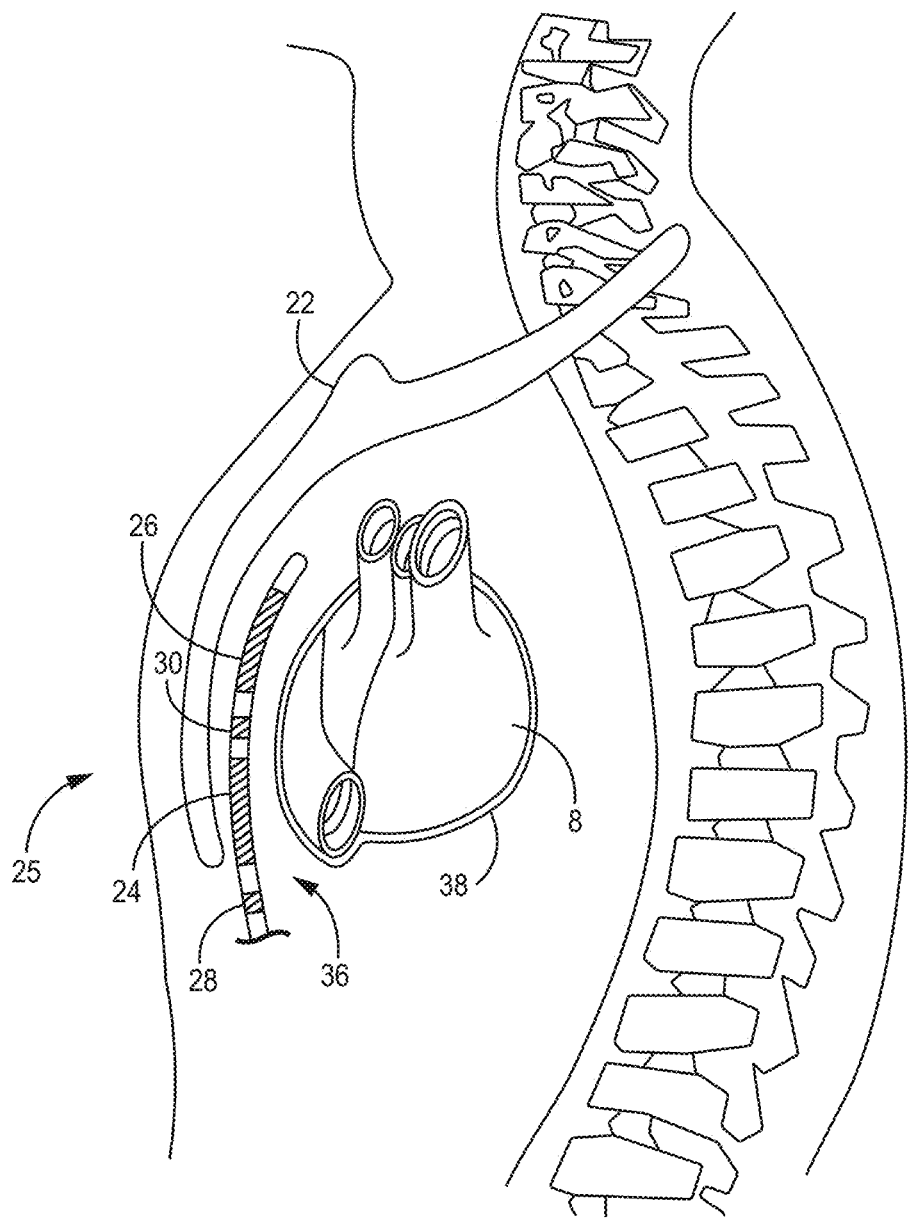
Figure 2C:
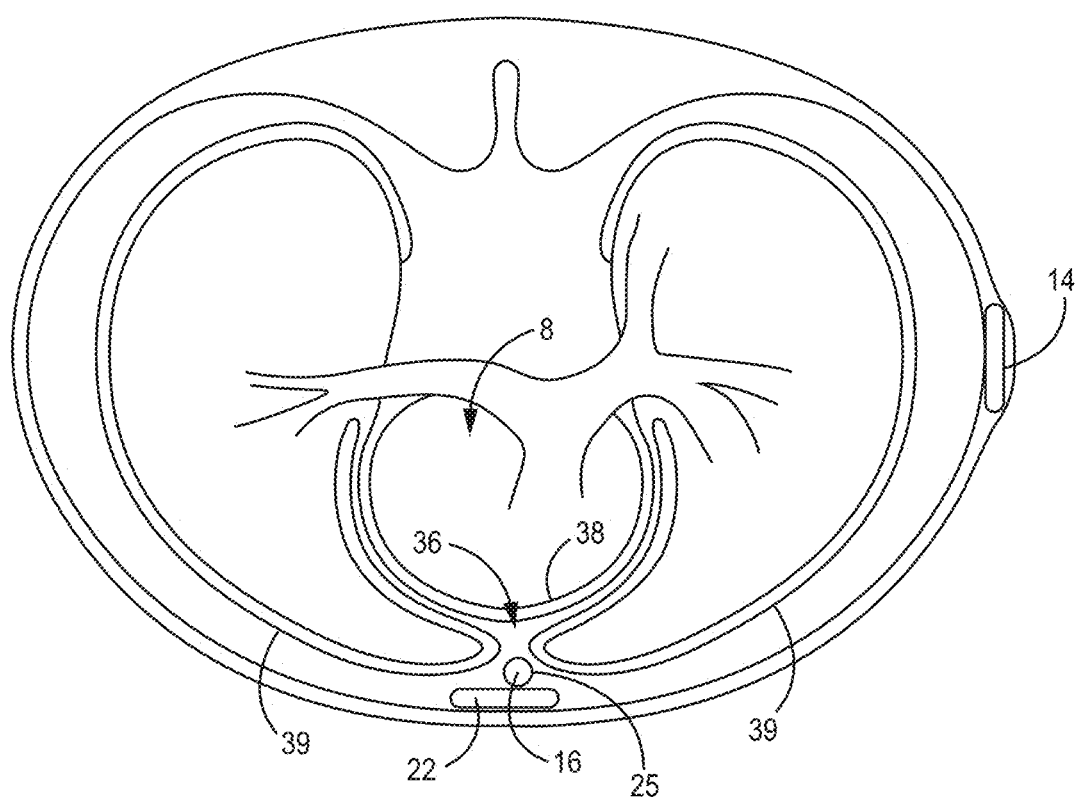

FIGS. 2A-2C are conceptual diagrams of patient 12 implanted with extra-cardiovascular ICD system 10 in a different implant configuration than the arrangement shown in FIGS. 1A-1B. FIG. 2A is a front view of patient 12 implanted with ICD system 10. FIG. 2B is a side view of patient 12 implanted with ICD system 10. FIG. 2C is a transverse view of patient 12 implanted with ICD system 10. In this arrangement, extra-cardiovascular lead 16 of system 10 is implanted at least partially underneath sternum 22 of patient 12. Lead 16 extends subcutaneously or submuscularly from ICD 14 toward xiphoid process 20 and at a location near xiphoid process 20 bends or turns and extends superiorly within anterior mediastinum 36 in a substernal position.

Anterior mediastinum 36 may be viewed as being bounded laterally by pleurae 39, posteriorly by pericardium 38, and anteriorly by sternum 22 (see FIG. 2C). The distal portion 25 of lead 16 may extend along the posterior side of sternum 22 substantially within the loose connective tissue and/or substernal musculature of anterior mediastinum 36. A lead implanted such that the distal portion 25 is substantially within anterior mediastinum 36, may be referred to as a "substernal lead."

In the example illustrated in FIGS. 2A-2C, lead 16 is located substantially centered under sternum 22. In other instances, however, lead 16 may be implanted such that it is offset laterally from the center of sternum 22. In some instances, lead 16 may extend laterally such that distal portion 25 of lead 16 is underneath/below the ribcage 32 in addition to or instead of sternum 22. In other examples, the distal portion 25 of lead 16 may be implanted in other extra-cardiovascular, intra-thoracic locations, including the pleural cavity or around the perimeter of and adjacent to but typically not within the pericardium 38 of heart 8. Other implant locations and lead and electrode arrangements that may be used in conjunction with the SVT discrimination techniques described herein are generally disclosed in the above-incorporated references.

Figure 3:
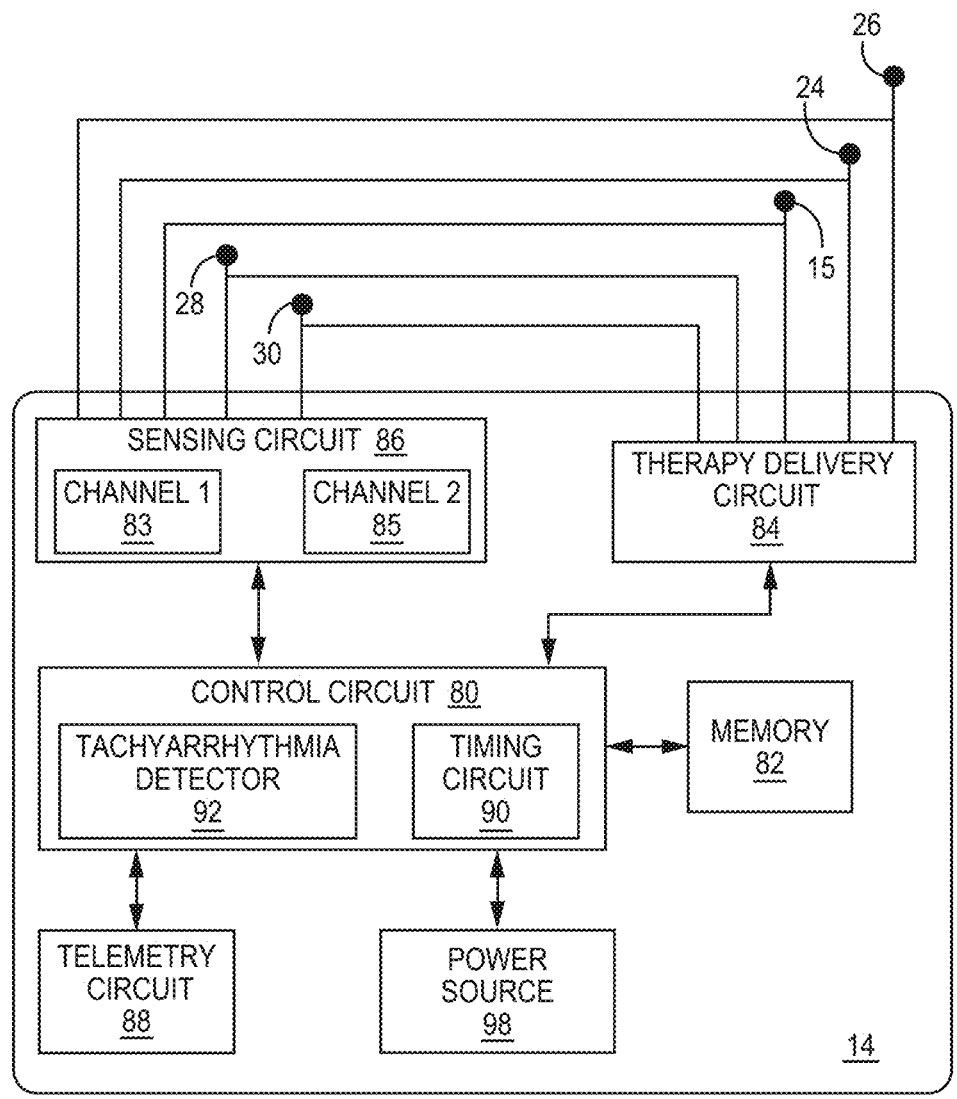
FIG. 3 is a schematic diagram of the ICD of FIGS. 1A-2C according to one example.

FIG. 3 is a schematic diagram of ICD 14 according to one example. The electronic circuitry enclosed within housing 15 (shown schematically as an electrode in FIG. 3) includes software, firmware and hardware that cooperatively monitor cardiac electrical signals, determine when an electrical stimulation therapy is necessary, and deliver therapies as needed according to programmed therapy delivery algorithms and control parameters. The software, firmware and hardware are configured to detect tachyarrhythmias and deliver anti-tachyarrhythmia therapy, e.g., detect ventricular tachyarrhythmias and in some cases discriminate VT from VF for determining when ATP or CV/DF shocks are required. ICD 14 is coupled to an extra-cardiovascular lead, such as lead 16 carrying extra-cardiovascular electrodes 24, 26, 28, and 30, for delivering electrical stimulation pulses to the patient's heart and for sensing cardiac electrical signals.

ICD 14 includes a control circuit 80, memory 82, therapy delivery circuit 84, sensing circuit 86, and telemetry circuit 88. A power source 98 provides power to the circuitry of ICD 14, including each of the components 80, 82, 84, 86, and 88 as needed. Power source 98 may include one or more energy storage devices, such as one or more rechargeable or non-rechargeable batteries. The connections between power source 98 and each of the other components 80, 82, 84, 86 and 88 are to be understood from the general block diagram of FIG. 3, but are not shown for the sake of clarity. For example, power source 98 may be coupled to one or more charging circuits included in therapy delivery circuit 84 for charging holding capacitors included in therapy delivery circuit 84 that are discharged at appropriate times under the control of control circuit 80 for producing electrical pulses according to a therapy protocol, such as for bradycardia pacing, post-shock pacing, ATP and/or CV/DF shock pulses. Power source 98 is also coupled to components of sensing circuit 86, such as sense amplifiers, analog-to-digital converters, switching circuitry, etc. as needed.

The functional blocks shown in FIG. 3 represent functionality included in ICD 14 and may include any discrete and/or integrated electronic circuit components that implement analog and/or digital circuits capable of producing the functions attributed to ICD 14 herein. The various components may include an application specific integrated circuit (ASIC), an electronic circuit, a processor (shared, dedicated, or group) and memory that execute one or more software or firmware programs, a combinational logic circuit, state machine, or other suitable components or combinations of components that provide the described functionality. The particular form of software, hardware and/or firmware employed to implement the functionality disclosed herein will be determined primarily by the particular system architecture employed in the ICD and by the particular detection and therapy delivery methodologies employed by the ICD. Providing software, hardware, and/or firmware to accomplish the described functionality in the context of any modern ICD system, given the disclosure herein, is within the abilities of one of skill in the art.

Memory 82 may include any volatile, non-volatile, magnetic, or electrical non-transitory computer readable storage media, such as random access memory (RAM), read-only memory (ROM), non-volatile RAM (NVRAM), electrically-erasable programmable ROM (EEPROM), flash memory, or any other memory device. Furthermore, memory 82 may include non-transitory computer readable media storing instructions that, when executed by one or more processing circuits, cause control circuit 80 and/or other ICD components to perform various functions attributed to ICD 14 or those ICD components. The non-transitory computer-readable media storing the instructions may include any of the media listed above.

The functions attributed to ICD 14 herein may be embodied as one or more integrated circuits. Depiction of different features as circuits is intended to highlight different functional aspects and does not necessarily imply that such circuits must be realized by separate hardware or software components. Rather, functionality associated with one or more circuits may be performed by separate hardware, firmware or software components, or integrated within common hardware, firmware or software components. For example, cardiac event sensing and tachyarrhythmia detection operations may be performed cooperatively by sensing circuit 86 and control circuit 80 and may include operations implemented in a processor or other signal processing circuitry included in control circuit 80 executing instructions stored in memory 82 and control signals such as blanking and timing intervals and sensing threshold amplitude signals sent from control circuit 80 to sensing circuit 86.

Control circuit 80 communicates, e.g., via a data bus, with therapy delivery circuit 84 and sensing circuit 86 for sensing cardiac electrical activity, detecting cardiac rhythms, and controlling delivery of cardiac electrical stimulation therapies in response to sensed cardiac signals. Therapy delivery circuit 84 and sensing circuit 86 are electrically coupled to electrodes 24, 26, 28, 30 carried by lead 16 and the housing 15, which may function as a common or ground electrode or as an active can electrode for delivering CV/DF shock pulses or cardiac pacing pulses.

Sensing circuit 86 may be selectively coupled to electrodes 28, 30 and/or housing 15 in order to monitor electrical activity of the patient's heart. Sensing circuit 86 may additionally be selectively coupled to defibrillation electrodes 24 and/or 26 for use in a sensing electrode vector together or in combination with one or more of electrodes 28, 30 and/or housing 15. Sensing circuit 86 may be enabled to selectively receive cardiac electrical signals from at least two sensing electrode vectors from the available electrodes 24, 26, 28, 30, and housing 15. At least two cardiac electrical signals from two different sensing electrode vectors may be received simultaneously by sensing circuit 86. Sensing circuit 86 may monitor one or both or the cardiac electrical signals at a time for sensing cardiac electrical events, e.g., P-waves attendant to the depolarization of the atrial myocardium and/or R-waves attendant to the depolarization of the ventricular myocardium, and providing digitized cardiac signal waveforms for analysis by control circuit 80. For example, sensing circuit 86 may include switching circuitry (not shown) for selecting which of electrodes 24, 26, 28, 30, and housing 15 are coupled to a first sensing channel 83 and which are coupled to a second sensing channel 85 of sensing circuit 86. Switching circuitry may include a switch array, switch matrix, multiplexer, or any other type of switching device suitable to selectively couple components of sensing circuit 86 to selected electrodes.

Each sensing channel 83 and 85 may be configured to amplify, filter and digitize the cardiac electrical signal received from selected electrodes coupled to the respective sensing channel to improve the signal quality for detecting cardiac electrical events, such as R-waves or performing other signal analysis. The cardiac event detection circuitry within sensing circuit 86 may include one or more sense amplifiers, filters, rectifiers, threshold detectors, comparators, analog-to-digital converters (ADCs), timers or other analog or digital components as described further in conjunction with FIG. 4. A cardiac event sensing threshold may be automatically adjusted by sensing circuit 86 under the control of control circuit 80, based on timing intervals and sensing threshold values determined by control circuit 80, stored in memory 82, and/or controlled by hardware, firmware and/or software of control circuit 80 and/or sensing circuit 86.

Upon detecting a cardiac electrical event based on a sensing threshold crossing, sensing circuit 86 may produce a sensed event signal, such as an R-wave sensed event signal, that is passed to control circuit 80. In some examples, the sensed event signal may be used by control circuit 80 to trigger storage of a segment of a cardiac electrical signal for analysis for confirming the R-wave sensed event signals and discriminating SVT as described below.

The R-wave sensed event signals are also used by control circuit 80 for determining ventricular event intervals, referred to herein as "RR intervals" or "RRIs" for detecting tachyarrhythmia and determining a need for therapy. A ventricular event interval or RRI is the time interval between two consecutively sensed R-waves and may be determined between two consecutive R-wave sensed event signals received from sensing circuit 86. In other words, a ventricular event interval or RRI is the time interval between a first R-wave and a second R-wave the immediately follows the first R-wave. For example, control circuit 80 may include a timing circuit 90 for determining RRIs between consecutive R-wave sensed event signals received from sensing circuit 86 and for controlling various timers and/or counters used to control the timing of therapy delivery by therapy delivery circuit 84. Timing circuit 90 may additionally set time windows such as morphology template windows, morphology analysis windows or perform other timing related functions of ICD 14 including synchronizing CV/DF shocks or other therapies delivered by therapy delivery circuit 84 with sensed cardiac events.

Tachyarrhythmia detector 92 is configured to analyze signals received from sensing circuit 86 for detecting tachyarrhythmia episodes. Tachyarrhythmia detector 92 may be implemented in control circuit 80 as software, hardware and/or firmware that processes and analyzes signals received from sensing circuit 86 for detecting VT and/or VF. In some examples, tachyarrhythmia detector 92 may include comparators and counters for counting RRIs determined by timing circuit 90 that fall into various rate detection zones for determining a ventricular rate or performing other rate- or interval-based assessments for detecting and discriminating VT and VF. For example, tachyarrhythmia detector 92 may compare the RRIs determined by timing circuit 90 to one or more tachyarrhythmia detection interval zones, such as a tachycardia detection interval zone and a fibrillation detection interval zone. RRIs falling into a detection interval zone are counted by a respective VT interval counter or VF interval counter and in some cases in a combined VT/VF interval counter included in tachyarrhythmia detector 92.

When a VT, VF, or combined VT/VF interval counter reaches a threshold count value, often referred to as "number of intervals to detect" or "NID," a ventricular tachyarrhythmia may be detected by control circuit 80. Tachyarrhythmia detector 92 may be configured to perform other signal analysis for determining if other detection criteria are satisfied before detecting VT or VF when an NID is reached however. For example, cardiac signal analysis may be performed to determine if R-wave morphology criteria, onset criteria, and noise and oversensing rejection criteria are satisfied in order to determine if the VT/VF detection should be made or withheld. As disclosed herein, tachyarrhythmia detector 92 may withhold the VT or VF detection when an NID is reached if analysis of cardiac signal waveform features indicates that the rhythm is an SVT rhythm. In particular, if criteria indicating that a fast ventricular rate is likely a rapidly conducted AF rhythm, a VT or VF detection based on the NID being reached may be rejected.

To support additional cardiac signal analyses performed by tachyarrhythmia detector 92, sensing circuit 86 may pass a digitized cardiac electrical signal to control circuit 80. A cardiac electrical signal from the selected sensing channel, e.g., from first sensing channel 83 and/or the second sensing channel 85, may be passed through a filter and amplifier, provided to a multiplexer and thereafter converted to multi-bit digital signals by an analog-to-digital converter, all included in sensing circuit 86, for storage in memory 82. This digitized cardiac electrical signal or segments thereof may be used by control circuit 80 to analyze amplitude and/or morphology information for use in SVT discrimination as described below.

Memory 82 may include read-only memory (ROM) in which stored programs controlling the operation of the control circuit 80 reside. Memory 82 may further include random access memory (RAM) or other memory devices configured as a number of recirculating buffers capable of holding a series of measured RRIs, counts or other data for analysis by the tachyarrhythmia detector 92. Memory 82 may be configured to store a predetermined number of cardiac electrical signal segments in circulating buffers under the control of control circuit 80. For instance, up to eight cardiac electrical signal segments each corresponding to an R-wave sensed event signal may be stored in memory 82. Additionally or alternatively, features derived from each of up to eight cardiac signal segments that each correspond to an R-wave sensed event signal may be buffered in memory 82 for use in SVT discrimination as described below.

Therapy delivery circuit 84 includes charging circuitry, one or more charge storage devices such as one or more high voltage capacitors and/or low voltage capacitors, and switching circuitry that controls when the capacitor(s) are discharged across a selected pacing electrode vector or CV/DF shock vector. Charging of capacitors to a programmed pulse amplitude and discharging of the capacitors for a programmed pulse width may be performed by therapy delivery circuit 84 according to control signals received from control circuit 80. Timing circuit 90 of control circuit 80 may include various timers or counters that control when ATP or other cardiac pacing pulses are delivered. For example, timing circuit 90 may include programmable digital counters set by a microprocessor of the control circuit 80 for controlling the basic pacing time intervals associated with various pacing modes or ATP sequences delivered by ICD 14. The microprocessor of control circuit 80 may also set the amplitude, pulse width, polarity or other characteristics of the cardiac pacing pulses, which may be based on programmed values stored in memory 82.

In response to detecting VT or VF, control circuit 80 may control therapy delivery circuit 84 to deliver therapies such as ATP and/or CV/DF therapy. Therapy can be delivered by initiating charging of high voltage capacitors via a charging circuit, both included in therapy delivery circuit 84. Charging is controlled by control circuit 80, which monitors the voltage on the high voltage capacitors passed to control circuit 80 via a charging control line. When the voltage reaches a predetermined value set by control circuit 80, a logic signal is generated on a capacitor full line and passed to therapy delivery circuit 84, terminating charging. A CV/DF pulse is delivered to the heart under the control of the timing circuit 90 by an output circuit of therapy delivery circuit 84 via a control bus. The output circuit may include an output capacitor through which the charged high voltage capacitor is discharged via switching circuitry, e.g., an H-bridge, which determines the electrodes used for delivering the cardioversion or defibrillation pulse and the pulse wave shape. In some examples, the high voltage therapy circuit configured to deliver CV/DF shock pulses can be controlled by control circuit 80 to deliver pacing pulses, e.g., for delivering ATP or post shock pacing pulses. In other examples, therapy delivery circuit 84 may include a low voltage therapy circuit for generating and delivering relatively lower voltage pacing pulses for a variety of pacing needs. Therapy delivery and control circuitry generally disclosed in any of the above-incorporated patents may be implemented in ICD 14.

It is recognized that aspects of the methods disclosed herein may be implemented in an implantable medical device that is used for monitoring cardiac electrical signals by sensing circuit 86 and control circuit 80 without having therapy delivery capabilities or in an implantable medical device that monitors cardiac electrical signals and delivers cardiac pacing therapies by therapy delivery circuit 84, without high voltage therapy capabilities, such as cardioversion/defibrillation shock capabilities or vice versa.

Control parameters utilized by control circuit 80 for detecting cardiac arrhythmias and controlling therapy delivery may be programmed into memory 82 via telemetry circuit 88. Telemetry circuit 88 includes a transceiver and antenna for communicating with external device 40 (shown in FIG. 1A) using RF communication or other communication protocols as described above. Under the control of control circuit 80, telemetry circuit 88 may receive downlink telemetry from and send uplink telemetry to external device 40. In some cases, telemetry circuit 88 may be used to transmit and receive communication signals to/from another medical device implanted in patient 12.

Figure 4:
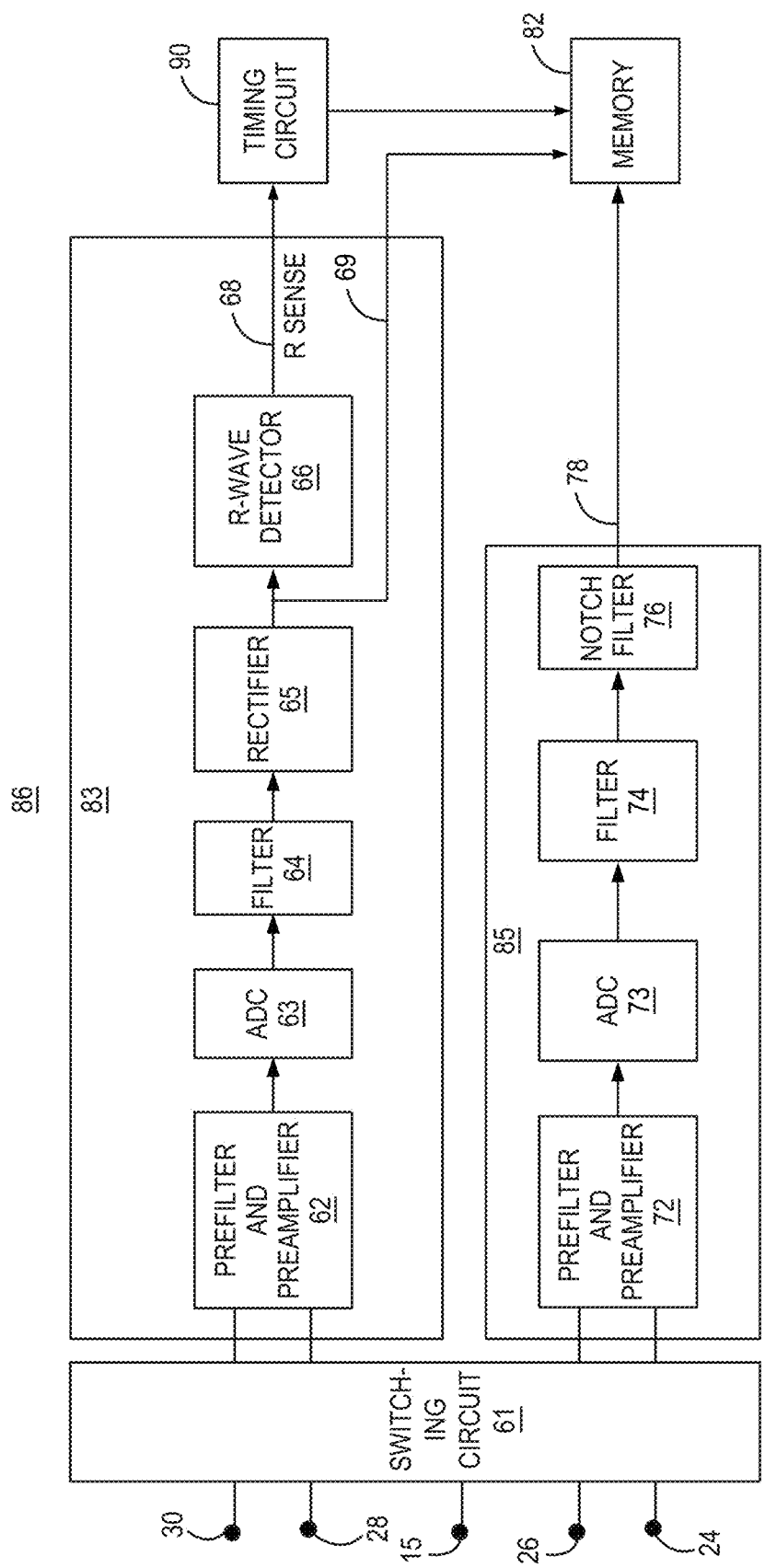
FIG. 4 is diagram of circuitry included in the sensing circuit of FIG. 3 according to one example.

FIG. 4 is a diagram of circuitry included in first sensing channel 83 and second sensing channel 85 of sensing circuit 86 according to one example. First sensing channel 83 may be selectively coupled via switching circuit 61 to a first sensing electrode vector including electrodes carried by extra-cardiovascular lead 16 as shown in FIG. 1A-1B or 2A-2C for receiving a first cardiac electrical signal. First sensing channel 83 may be coupled to a sensing electrode vector that is a short bipole, having a relatively shorter inter-electrode distance or spacing than the second electrode vector coupled to second sensing channel 85. For example, the first sensing electrode vector may include pace/sense electrodes 28 and 30. In other examples, the first sensing electrode vector coupled to sensing channel 83 may include a defibrillation electrode 24 and/or 26, e.g., a sensing electrode vector between pace/sense electrode 28 and defibrillation electrode 24 or between pace/sense electrode 30 and either of defibrillation electrodes 24 or 26. In still other examples, the first sensing electrode vector may be between defibrillation electrodes 24 and 26.

In some patients, a bipole between electrodes carried by lead 16 may result in patient body posture dependent changes in the cardiac electrical signal as the sensing vector of the bipole relative to the cardiac axis changes with changes in patient body posture or body motion. Accordingly, the sensing electrode vector coupled to the first sensing channel 83 may include housing 15 and any of the electrodes 24, 26, 28 and 30 carried by lead 16. A relatively longer bipole including housing 15 and a lead-based electrode may be less sensitive to positional changes. Cardiac electrical signals received via extra-cardiovascular electrodes may be more influenced by positional changes of the patient than electrodes carried by transvenous leads. The amplitude, polarity, and wave shape of R-waves may change, for example, as patient posture changes. As a result, R-wave morphology analysis performed to discriminate between SVT, such as rapidly conducted AF, and VT/VF may lead to false VT/VF detection when R-wave amplitude and/or morphology has changed due to positional changes of the patient. The techniques disclosed herein may be used to detect and discriminate SVT to avoid false detection of VT and VF and unnecessary electrical stimulation therapies even when patient posture changes cause changes in QRS amplitude and morphology.

Sensing circuit 86 includes a second sensing channel 85 that receives a second cardiac electrical signal. The second cardiac electrical signal may be received from a second sensing vector, for example from a vector that includes a pace/sense electrode 28 or 30 paired with housing 15. Second sensing channel 85 may be selectively coupled to other sensing electrode vectors, which may form a relatively long bipole having an inter-electrode distance or spacing that is greater than the sensing electrode vector coupled to first sensing channel 83 in some examples. As described below, the second cardiac electrical signal received by second sensing channel 85 via a long bipole may be used by control circuit 80 for morphology analysis and for determining cardiac signal segment features for use in SVT discrimination. In other examples, any vector selected from the available electrodes, e.g., electrodes 24, 26, 28, 30 and/or housing 15, may be included in a sensing electrode vector coupled to second sensing channel 85. The sensing electrode vectors coupled to first sensing channel 83 and second sensing channel 85 are typically different sensing electrode vectors, which may have no common electrodes or only one common electrode but not both. In some instances, however, first sensing channel 83 and second sensing channel 85 may be coupled to the same sensing electrode vector. In this case, some of the circuitry for first and second sensing channels may be common, such as pre-filter and pre-amplifier circuits 62, 72, ADCs 63, 73 and filters 64, 74.

In the illustrative example shown in FIG. 4, the electrical signals developed across a first sensing electrode vector are received by sensing channel 83 and electrical signals developed across a second sensing electrode vector are received by sensing channel 85. The cardiac electrical signals are provided as differential input signals to the pre-filter and pre-amplifiers 62 and 72, respectively, of first sensing channel 83 and second sensing channel 85. Non-physiological high frequency and DC signals may be filtered by a low pass or bandpass filter included in each of pre-filter and pre-amplifiers 62 and 72, and high voltage signals may be removed by protection diodes included in pre-filter and pre-amplifiers 62 and 72. Pre-filter and pre-amplifiers 62 and 72 may amplify the pre-filtered signal by a gain of between 10 and 100, in one example a gain of 17.5, and may convert the differential signal to a single-ended output signal that is passed to analog-to-digital converter (ADC) 63 in first sensing channel 83 and to ADC 73 in second sensing channel 85. Pre-filter and preamplifiers 62 and 72 may provide anti-alias filtering and noise reduction prior to digitization.

ADC 63 and ADC 73, respectively, convert the first cardiac electrical signal from an analog signal to a first digital bit stream and the second cardiac electrical signal to a second digital bit stream. In one example, ADC 63 and ADC 73 may be sigma-delta converters (SDC), but other types of ADCs may be used. In some examples, the outputs of ADC 63 and ADC 73 may be provided to decimators (not shown), which function as digital low-pass filters that increase the resolution and reduce the sampling rate of the respective first and second cardiac electrical signals.

In first sensing channel 83, the digital output of ADC 63 is passed to filter 64 which may be a digital bandpass filter having a bandpass of approximately 10 Hz to 30 Hz for passing cardiac electrical signals such as R-waves typically occurring in this frequency range. The bandpass filtered signal is passed from filter 64 to rectifier 65 then to R-wave detector 66. In some examples, the filtered, digitized cardiac electrical signal 69 from sensing channel 83, e.g., output of filter 64 or rectifier 65, may be stored in memory 82 for signal processing by control circuit 80 for use in detecting and discriminating tachyarrhythmia episodes. The output signal 69 may be passed from sensing circuit 86 to memory 82 under the control of control circuit 80 for storing segments of the first cardiac electrical signal in temporary buffers of memory 82. For example, timing circuit 90 of control circuit 80 may set a time interval or number of sample points relative to an R-wave sensed event signal 68 received from R-wave detector 66, over which the segment of the first digitized cardiac electrical signal 69 is stored in memory 82. The buffered, first cardiac electrical signal segment may be analyzed by control circuit 80 on a triggered, as needed basis for determining cardiac signal segment features for discriminating SVT and withholding an interval-based VT or VF detection, even when other R-wave morphology analysis meets VT/VF detection criteria. As described below, analysis of the first cardiac electrical signal segment may be performed for determining if a pause in fast RRIs is detected as evidence of SVT, e.g., as evidence of a rapidly conducted AF rhythm. If such a pause is detected, tachyarrhythmia detector 92 of control circuit 80 may withhold or delay detection of VT/VF.

R-wave detector 66 may include an auto-adjusting sense amplifier, comparator and/or other detection circuitry that compares the filtered and rectified first cardiac electrical signal to an R-wave sensing threshold in real time and produces an R-wave sensed event signal 68 when the cardiac electrical signal crosses the R-wave sensing threshold outside of a post-sense blanking period.

The R-wave sensing threshold, controlled by sensing circuit 86 and/or control circuit 80, may be a multi-level sensing threshold as disclosed in pending U.S. Publication No. 2017/0312534 (Cao, et al.), incorporated herein by reference in its entirety. Briefly, the multi-level sensing threshold may have a starting sensing threshold value held for a time interval, which may be equal to a tachycardia detection interval or expected R-wave to T-wave interval, then drops to a second sensing threshold value held until a drop time interval expires, which may be 1 to 2 seconds long. The sensing threshold drops to a minimum sensing threshold, which may correspond to a programmed sensitivity, after the drop time interval. In other examples, the R-wave sensing threshold used by R-wave detector 66 may be set to a starting value based on the most-recently sensed R-wave peak amplitude and decay linearly or exponentially over time until reaching a minimum sensing threshold. The techniques described herein are not limited to a specific behavior of the sensing threshold. Instead, other decaying, step-wise adjusted or other automatically adjusted sensing thresholds may be utilized.

The second cardiac electrical signal, digitized by ADC 73 of sensing channel 85, may be passed to filter 74 for bandpass filtering. In some examples, filter 74 is a wideband filter for passing frequencies from 1 to 30 Hz or higher. In some examples, sensing channel 85 includes notch filter 76. Notch filter 76 may be implemented in firmware or hardware to attenuate 50 Hz or 60 Hz electrical noise in the second cardiac electrical signal. Cardiac electrical signals acquired using extra-cardiovascular electrodes may be more susceptible to 50 to 60 Hz electrical noise than transvenous or intra-cardiac electrodes, muscle noise and other EMI, electrical noise or artifacts. As such, notch filter 76 may be provided to significantly attenuate the magnitude of signals in the range of 50-60 Hz with minimum attenuation of signals in the range of approximately 1-30 Hz, corresponding to typical cardiac electrical signal frequencies.

The output signal 78 of notch filter 76 may be passed from sensing circuit 86 to memory 82 under the control of control circuit 80 for storing segments of the second cardiac electrical signal 78 in temporary buffers of memory 82. For example, timing circuit 90 of control circuit 80 may set a time interval or number of sample points relative to an R-wave sensed event signal 68 received from first sensing channel 83, over which the second cardiac electrical signal 78 is stored in memory 82. The buffered, second cardiac electrical signal segment may be analyzed by control circuit 80 on a triggered, as needed basis for determining cardiac signal segment features for discriminating SVT and withholding an interval-based VT or VF detection, even when other R-wave morphology analysis meets VT/VF detection criteria. As described below, analysis of the second cardiac electrical signal segment may be performed for determining if a pause in fast RRIs is detected as evidence of SVT, e.g., as evidence of a rapidly conducted AF rhythm. If such a pause is detected, tachyarrhythmia detector 92 of control circuit 80 may withhold or delay detection of VT/VF.

Notch filter 76 may be implemented as a digital filter for real-time filtering performed by firmware as part of sensing channel 85 or by control circuit 80 for filtering the buffered digital output of filter 74. In some examples, the output of filter 74 of sensing channel 85 may be stored in memory 82 in time segments defined relative to an R-wave sensed event signal 68 prior to filtering by notch filter 76. When control circuit 80 is triggered to buffer and analyze segments of the second cardiac electrical signal, for example as described in conjunction with FIG. 7, the notch filter 76 may be applied to the second cardiac electrical signal before morphology analysis and determination of cardiac signal segment features used for SVT discrimination.

The configuration of sensing channels 83 and 85 shown in FIG. 4 is illustrative in nature and should not be considered limiting of the techniques described herein. The sensing channels 83 and 85 of sensing circuit 86 may include more or fewer components than illustrated and described in FIG. 4. First sensing channel 83 may be configured to detect R-waves from a first cardiac electrical signal in real time, e.g., in hardware implemented components, based on crossings of an R-wave sensing threshold by the first cardiac electrical signal, and second sensing channel 85 may be configured to provide a second cardiac electrical signal for storage in memory 82 for processing and analysis by control circuit 80 for determining if the signal waveform morphology corresponding to a sensed R-wave in the first sensing channel is indicative of VT or VF or if the signal waveform features support an SVT detection and withholding of VT or VF detection. In other examples, both sensing channels 83 and 85 may be capable of sensing R-waves in real time and/or both channels 83 and 85 may provide a digitized cardiac signal for buffering in memory 82 for morphological signal analysis during VT/VF detection algorithms. In still other examples, sensing circuit 86 may include only a single sensing channel.

Figure 5:
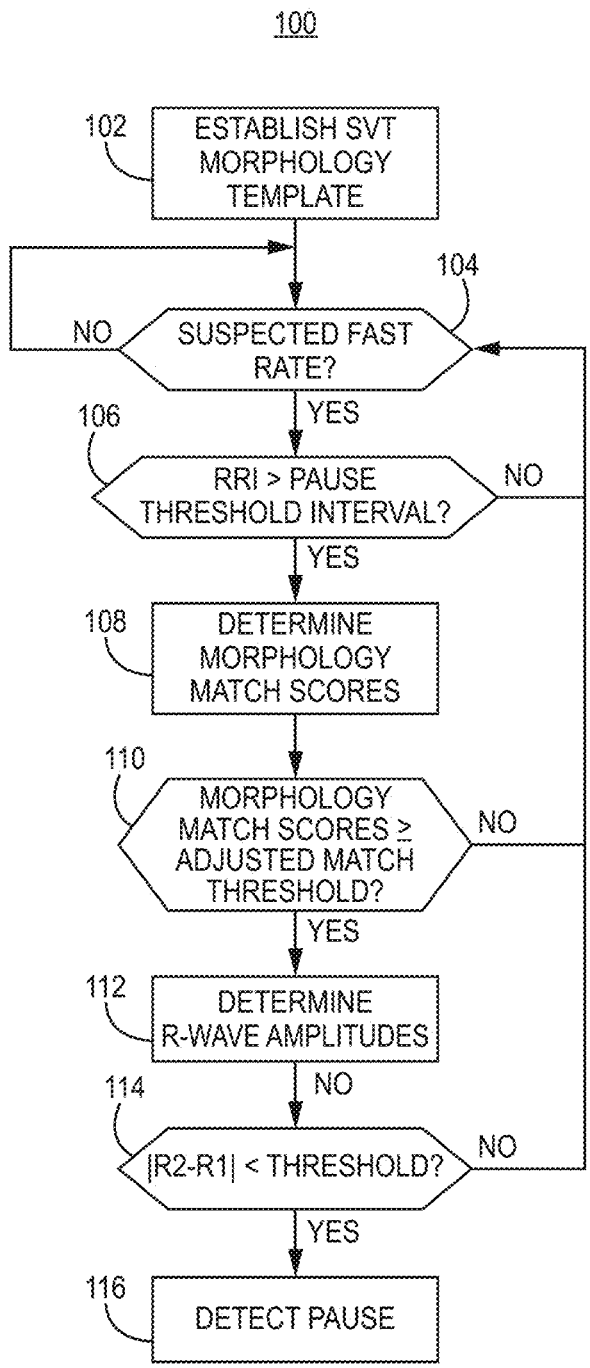
FIG. 5 is a flow chart of a method performed by an ICD for detecting a pause in a rapidly conducted AF rhythm.

FIG. 5 is a flow chart 100 of a method performed by ICD 14 for detecting a pause in a fast ventricular rate. As described herein, the detected pause may be evidence of a rapidly conducted AF rhythm, a type of SVT that may be inadvertently detected as a ventricular tachyarrhythmia. AF that is conducted to the ventricles results in short, irregular RRIs that may be falsely detected as a ventricular tachyarrhythmia. Discrimination of rapidly conducted AF from a true ventricular tachyarrhythmia may be based on detecting a pause in the conducted rhythm. A pause in the conducted rhythm is a relatively long RRI during a fast ventricular rate, which may occur when an atrial fibrillation wave is not conducted to the ventricles due to a state of refractoriness of the ventricular myocardium and inherent conduction delays in the intrinsic cardiac conduction system. By detecting a pause in the conducted AF rhythm, an improper ventricular tachyarrhythmia detection may be withheld.

At block 102, control circuit 80 establishes an SVT morphology template representative of the expected R-wave morphology during an SVT. The SVT morphology template is therefore also referred to herein as an "R-wave template." The SVT morphology template may be established according to techniques generally disclosed in the above-incorporated U.S. Pat. No. 6,393,316 (Gillberg, et al.), and in U.S. Pat. Pub. No. 2018/0303368 (Zhang, et al.), incorporated herein by reference in its entirety. The SVT morphology template represents the expected R-wave morphology during a supraventricular rhythm, which may be a sinus rhythm or an atrial tachyarrhythmia that is conducted to the ventricles. The SVT morphology template may be acquired during a slow, non-paced ventricular rhythm to represent a QRS waveform arising from the sinus node and is not necessarily acquired during supraventricular tachycardia. In other examples, the SVT morphology template may be acquired during sinus tachycardia, for example during patient exercise. The SVT morphology template represents the QRS waveform morphology expected when the ventricular depolarization is conducted to the ventricles from the atria via the intrinsic ventricular conduction system (e.g., His bundle and Purkinje fibers).

Control circuit 80 may be configured to analyze cardiac electrical signals for detecting a pause in a conducted AF rhythm after first determining that a fast ventricular rate is suspected. At block 104, control circuit 80 determines that a plurality of sensed ventricular events meet a fast ventricular rate criteria. In one example, control circuit 80 may determine that the plurality of sensed ventricular events meet the fast ventricular rate criteria in response to detecting a predetermined number of RRIs determined using the plurality of sensed ventricular events are characterized as ventricular tachycardia detection intervals (TDIs), a predetermined number of ventricular fibrillation detection intervals (FDIs), or a predetermined number of a combination of TDIs and FDIs. TDIs and FDIs are detected as RRIs that are less than a respective TDI threshold and FDI threshold. For example, the TDI threshold may be programmable between 280 and 650 ms, e.g., set nominally to 360 ms. The FDI threshold may be programmable between 240 ms and 400 ms, e.g., set nominally to 320 ms.

The RRIs compared to the TDI threshold and the FDI threshold are determined based on R-wave sensed event signals produced by sensing circuit 86 in response to the first sensing channel 83 detecting an R-wave sensing threshold crossing by the first cardiac electrical signal outside of a blanking period. The R-wave sensed event signal may be passed to control circuit 80. In response to the R-wave sensed event signal, timing circuit 90 of control circuit 80 determines an RRI ending with the current R-wave sensed event signal and beginning with the most recent preceding R-wave sensed event signal. The timing circuit 90 of control circuit 80 may pass the RRI timing information to the tachyarrhythmia detection circuit 92 which adjusts tachyarrhythmia interval counters, e.g., VT, VF or VT/VF interval counters, based on the RRI.

If the RRI is shorter than the TDI threshold but longer than the FDI threshold, i.e., if the RRI is in a VT detection interval zone, a VT interval counter is increased. The VT interval counter may be configured to count consecutive VT intervals for detecting VT in which case the VT interval counter may be reset to zero if the RRI is longer than the TDI. In other instances, the VT interval counter may be configured to count VT intervals that occur within a particular time window, e.g., within a particular period of time or within a particular number of beats or RRI intervals (X of Y). If the RRI is shorter than the FDI, the VF counter is increased. The VF counter may be a probabilistic VF counter that counts VF intervals in an X of Y manner such that VF may be detected when a threshold number of VF intervals are detected which are not required to be consecutive. In some examples, a combined VT/VF interval counter is increased if the RRI is less than the TDI. In some cases, VT detection may be disabled such that the suspected fast rate is detected at block 104 based only on a predetermined number of FDIs.

After updating the tachyarrhythmia interval counters, tachyarrhythmia detector 92 compares the VT and VF interval counter values (and optionally a combined VT and VF interval counter) to a suspected fast rate threshold at block 104. The suspected fast rate threshold values are less than the respective VT NID and VF NID required in order to detect VT or VF, respectively. Different fast heart rate thresholds may be applied to the VT interval counter and the VF interval counter. The suspected fast rate threshold may be a count of at least two TDIs or a count of at least three FDIs in one example. The fast heart rate threshold may be a value of one or more. In other examples, the fast heart rate threshold is a higher number, for example five or higher, but may be less than the NID required to detect VT or VF.

If a VT interval counter, a VF interval counter, or a combined VT and VF interval counter reaches the fast rate threshold set for the respective counter, "yes" branch of block 104, control circuit 80 detects a suspected fast ventricular rate and may enable analysis on an event by event basis for detecting a pause in the fast rate of sensed R-waves that is evidence of a rapidly conducted AF rhythm. In response to detecting the suspected fast rate of ventricular events at block 104, the RRI ending with the currently sensed R-wave is compared to a pause threshold interval at block 106. If the RRI is not greater than the pause threshold interval, a pause is not detected. Control circuit 80 continues to compare RRIs to the pause threshold interval on a beat by beat basis as long as the suspected fast rate criteria are met at block 104. The RRI determined at block 106 and compared to the pause threshold interval may be based on R-wave sensed event signals received from the first sensing channel 83 based on R-wave sensing threshold crossings of the first cardiac electrical signal. In other examples, however, the RRI determined at block 106 and compared to the pause threshold interval may be based on a cardiac electrical signal received by the second sensing channel 85.

The pause threshold interval may be set to be equal to the TDI when VT detection is enabled. If VT detection is not enabled, the pause threshold interval may be set to be equal to the FDI. In some examples, control circuit 80 may establish an SVT limit as a minimum median RRI for which an SVT can be detected or a VT/VF detection can be withheld. The SVT limit may be established as a programmed parameter stored in memory 82. In some examples, if the median RRI out of a sequence of a predetermined number of RRIs is less than the SVT limit, SVT detection cannot be made and cannot cause withholding of a VT or VF detection. For example, the SVT limit may be programmable and set between 210 and 310 ms. A nominal SVT limit may be 260 ms. If the median RRI determined from the most recent 12 RRIs, or other predetermined number of RRIs, is less than the SVT limit, an SVT is not detected, and any SVT detection related criteria are not used to withhold a VT or VF detection. In the process shown in FIG. 5, the SVT limit may be used in setting the pause threshold interval. The pause threshold interval may be set to the largest of the SVT limit and the TDI when VT detection is enabled or the largest of the SVT limit and the FDI plus an offset interval, e.g., FDI plus 20 ms, when VT detection is disabled.

If the current RRI is greater than the pause threshold interval at block 106, the control circuit 80 advances to block 108 to determine a morphology match score for each of the starting and trailing R-waves of the current RRI that is greater than the pause threshold interval. In one example, the QRS signal is buffered from a second cardiac electrical signal received from the second sensing channel 85 and notch filtered prior to determining the morphology match score. An R-wave sensed event signal received from the first sensing channel 83 may be used as a timing marker for selecting the beginning and ending sample points stored from the second cardiac electrical signal for buffering a cardiac signal segment corresponding to each of the starting and trailing R-waves of the RRI greater than the pause threshold interval. In this way, the first sensing channel 83 may be used for sensing R-waves, and the second sensing channel 85 may be used for acquiring cardiac signal segments from a different sensing vector that are compared to the SVT morphology template for determining a morphology match score at block 108. In another example, both the sensing R-waves and acquiring cardiac signal segments that are compared to the SVT morphology template for determining a morphology match score may be from the same sensing vector, such as the first sensing vector. In this case, the second cardiac electrical signal may be a segment of the cardiac electrical signal occurring after the detection of the fast ventricular rate.

The morphology match score may be determined using a wavelet transform analysis, e.g., as described in the above-incorporated Gillberg patent. In one example, 48 sample points of the digitized, notch-filtered cardiac electrical signal buffered from the second cardiac electrical signal may be processed to determine Haar wavelet-domain coefficients. The coefficients are compared to corresponding coefficients of the previously established SVT morphology template. Differences between the coefficients are determined and summed to determine the morphology matching score as percentage with a maximum possible score of 100.

Control circuit 80 compares morphology match scores of the starting and trailing R-waves of the RRI greater than the pause threshold interval to an adjusted match threshold at block 110. The morphology match threshold applied at block 110 is referred to as an "adjusted" match threshold because it may be different than a match threshold used by tachyarrhythmia detector 92 for identifying SVT beats as a part of other parts of the overall VT/VF detection algorithm. For example, when a suspected fast rate is detected, a match score may be determined by comparing R-wave morphology on a beat-by-beat basis to detect SVT beats. If a predetermined number of SVT beats are detected out of the most recent sensed R-waves, for example if 3 or more SVT beats are detected out of the most recent 8 sensed R-waves based on comparing the morphology matching score to the match threshold, an SVT rejection rule may be enabled so that if the VT or VF NID is reached based on RRIs, the VT or VF detection is withheld. A process for detecting SVT beats on a beat-by-beat basis for determining the status of an SVT rejection rule after suspected fast rate criteria are met is generally described in the above-incorporated U.S. Pat. Pub. No. 2018/0028087 and in U.S. Pat. Pub. No. 2018/0028085 (Zhang, et al.). The match threshold used to detect and count SVT beats may be different than the match threshold applied at block 110 for detecting a pause in a conducted AF rhythm. Detection of SVT beats using a first match threshold may be used to set a beat morphology rejection rule. The beat morphology rejection rule may be satisfied when a minimum number of morphology match scores out of a predetermined number of most recent morphology match scores exceed the first match score threshold in one example. For example, if at least three out of eight of the most recent morphology match scores exceed a match score threshold of 49, 61, 70 or other score threshold (out of a possible score of 100), the beat morphology rejection rule is satisfied. A relatively high match score, exceeding a selected match score threshold, indicates that an unknown beat during a fast rhythm matches the known SVT morphology template and is therefore an R-wave conducted from the atria rather than a VT or VF beat originating in the ventricles.

In order to detect a pause that is evidence of a rapidly conducted AF rhythm, control circuit 80 may determine an adjusted match threshold at block 110 and compare the adjusted match threshold to the morphology match score of the starting and trailing R-waves of each RRI greater than the pause threshold interval at block 110. The adjusted match threshold is adjusted from the first match threshold used to detect SVT beats based on QRS morphology. The adjusted match threshold may be decreased from the first, SVT beat match threshold by a predetermined percentage or decrement to allow an SVT morphology template match at a slightly lower match score than that required to detect an SVT beat. In some examples, the percentage used to adjust the first match threshold for detecting an SVT beat to an adjusted match threshold used for pause detection may be dependent on the programmed first match threshold. For example, the percentage may be scaled so that a higher percentage is used to adjust the first match threshold set to a higher value and a lower percentage is used to adjust the first match threshold set to a relatively lower value.

To illustrate, if the first, SVT beat detection match threshold is set to 70 or higher, it may be adjusted by decreasing it by 10% to obtain the adjusted, pause detection match threshold. If the first SVT beat detection match threshold is set to 61 or higher but less than 70, control circuit 80 may be decrease the first match threshold by 7% to obtain the adjusted match threshold for pause detection at block 110. If the first SVT beat detection match threshold is set to less than 61, it is decreased by only 4% to obtain the adjusted pause detection match threshold. In other examples, the adjusted pause detection match threshold may be a fixed decrement below the first match threshold used for SVT beat detection, which may or may not be scaled relative to the value of the first match threshold.

If one or both of the starting and trailing R-waves defining the RRI have a morphology match score that is less than the adjusted match threshold at block 110, "no" branch of block 110, a pause is not detected. The process returns to block 104. If both of the starting and trailing R-waves defining the RRI have a morphology match score that is greater than or equal to the adjusted match threshold at block 110, control circuit 80 may detect a pause as evidence of a conducted AF rhythm. In the example of FIG. 5, however, additional criteria for detecting the pause are required to be met. These additional criteria may be used in some examples. In other examples, the method may stop after detecting the pause based on the RRI being greater than the pause interval threshold and both of the starting and trailing R-waves defining the RRI having a morphology match score that is greater than or equal to the adjusted match threshold.

At block 112, control circuit 80 determines the R-wave amplitudes of the starting and trailing R-waves. The R-wave amplitudes may be determined from the first cardiac electrical signal. In other instances, the R-wave amplitudes may be determined from the second cardiac electrical signal sensed by second sensing channel 85. If the absolute difference between the R-wave amplitudes (R2−R1 where R2 is the trailing R-wave and R1 is the starting R-wave of the RRI that is greater than the pause threshold interval) is less than a difference threshold at block 114, control circuit 80 detects a pause at block 116. The difference threshold may be predefined or set based on the amplitude of either the starting or the trailing R-wave. In one example, the difference threshold is set to one half of the trailing R-wave amplitude.

The pause detected at block 116 by control circuit 80 based on the first and, in some instances, second cardiac electrical signal analysis may be evidence of a rapidly conducted AF rhythm. As described below, control circuit 80 may track the number of pauses detected over a predetermined number of sensed R-waves as long as the suspected fast rate criteria (block 104) are satisfied. If the NID for VT or VF detection is reached, at least one detected pause may cause control circuit 80 to withhold the VT or VF detection. In other instances, control circuit may need to detect more than one pause to withhold VT or VT detection.

Figure 6:
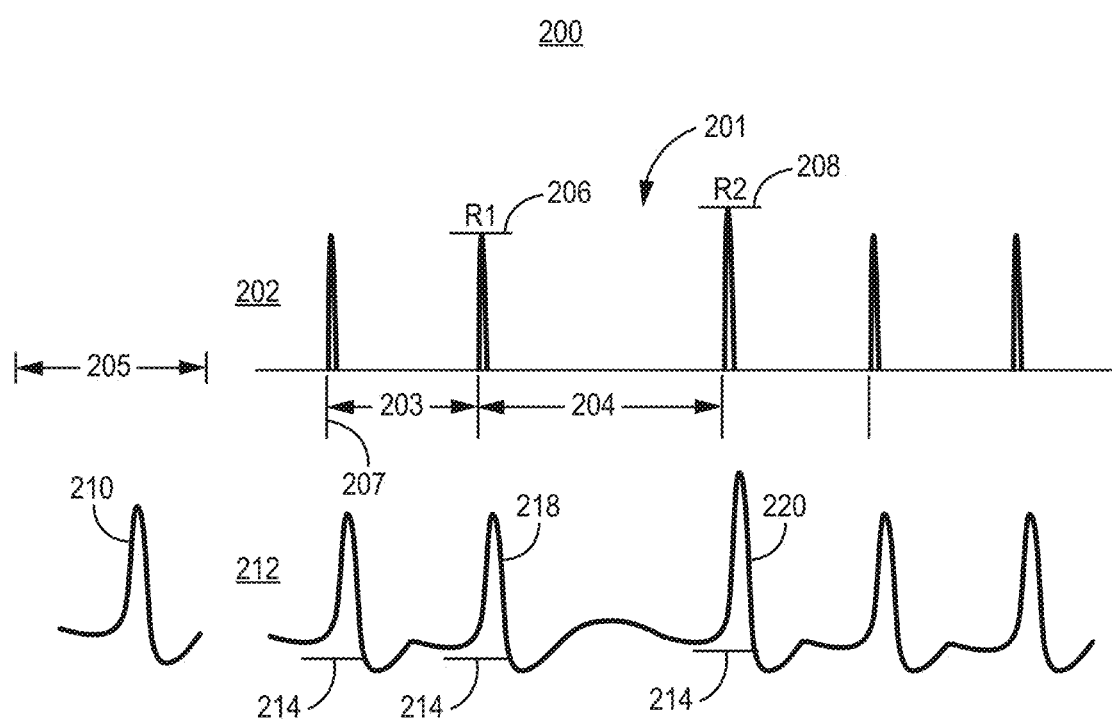
FIG. 6 is a conceptual diagram of a pause in a conducted AF rhythm that may be detected by an ICD.

FIG. 6 is a conceptual diagram 200 of a pause 201 in a fast rate of the sensed cardiac events that may be detected by control circuit 80. A first cardiac electrical signal 202 represents a filtered and rectified signal produced by the first sensing channel 83, and passed to R-wave detector 66, for producing R-wave sensed event signals 207. The second cardiac electrical signal 212 represents a signal produced by the second sensing channel 85, such as cardiac electrical signal 78 of FIG. 4. In other instances, second cardiac electrical signal 212 may represent a signal produced by the first sensing channel 83, such as cardiac electrical signal 69 output from rectifier 65 or a cardiac electrical signal output from filter 64.

Control circuit 80 determines RRIs 203 and 204 between consecutive R-wave sensed event signals 207. If the suspected fast heart rate criteria become satisfied, e.g., based on a threshold count of VT and/or VF intervals, as described above, control circuit 80 compares each RRI to a pause threshold interval 205 as long as the suspected fast heart rate criteria are satisfied. The first RRI 203 shown in FIG. 6 is shorter than the pause threshold interval 205. In some examples, no further analysis of the first and second cardiac signals 202 and 212 is performed for detecting a pause if the RRI 203 is less than the pause threshold interval 205.

The next RRI interval 204 is longer than the pause threshold interval 205. In response to the RRI interval 204 being longer than the pause threshold interval 205, control circuit 80 may determine the R-wave amplitude 206 of the starting R-wave (R1) of RRI 204 and the R-wave amplitude 208 of the trailing R-wave (R2) of RRI 204. The absolute difference between R1 amplitude 206 and R2 amplitude 208 is compared to a difference threshold. The difference threshold may be a defined value or set to a percentage of the R1 or R2 amplitude. In one example, the difference threshold is set to half of the R2 amplitude 208. If the R1 and R2 amplitudes 206 and 208 are within a difference threshold of each other, criteria for detecting RRI 204 as a pause in a suspected fast heart rate may be satisfied. R-wave amplitudes 206 and 208 are determined based on first cardiac electrical signal 202 in this example. However, in other examples, R-wave amplitudes 206 and 208 may be determined based on the digitized and filtered signals of either first sensing channel 83 (e.g., output signal 69 or an output signal of filter 64) or second sensing channel 85 (e.g., output signal 78).

In some examples, control circuit 80 may additionally or alternatively determine a morphology match score of the starting R-wave 218 and the trailing R-wave 220 of the second cardiac electrical signal 212 in response to RRI 204 being greater than the pause threshold interval 205. After the suspected fast rate criteria are met, e.g., when the TDI count reaches two or the FDI count reaches three, cardiac signal segments from the second cardiac electrical signal 212 are buffered over a time interval 214 set in response to each respective R-wave sensed event signal 207 from the first sensing channel 83. The cardiac signal segment acquired over the time interval 214 and corresponding to the starting R-wave 218 may be processed to determine wavelet coefficients that are compared to analogous wavelet coefficients of the SVT morphology template 210 to determine a morphology match score. As described above, the SVT morphology template 210 is previously established to represent the QRS morphology during an SVT rhythm. The cardiac signal segment over the time interval 214 and corresponding to the trailing R-wave 220 is also processed to determine a morphology match score from a comparison between the morphology of R-wave 220 and the SVT morphology template 210. In other examples, control circuit 80 determines a morphology match score of the starting R-wave 218 and the trailing R-wave 220 based on the digitized and filtered signals of the first sensing channel 83 (e.g., an output signal of filter 64).

The morphology match scores of R-wave 218 and R-wave 220 may each be compared to an adjusted match threshold as described above. If both match scores are greater than or equal to the adjusted match threshold, and all other criteria for detecting a pause are satisfied, RRI 204 is detected by control circuit 80 as a pause 201 in the fast heart rate. In some examples, control circuit 80 includes a counter configured to count the number of pause detections out of the most recent Y RRIs, for example out of the most recent twenty RRIs. If the VT NID or VF NID is reached and at least one pause has been detected in the most recent twenty RRIs, the VT or VF detection may be withheld. As described below, other criteria may be required to be satisfied in addition to a threshold number of detected pauses in order to withhold a VT or VF detection based on evidence of a rapidly conducted AF rhythm.

Control circuit 80 may detect the pause using the RRI interval length alone in some instances. In other instances, control circuit 80 may detect the pause using the RRI interval length in conjunction with one or both of the amplitude or morphology associated with the starting and trailing R-waves meeting the pause criteria.

Figure 7:
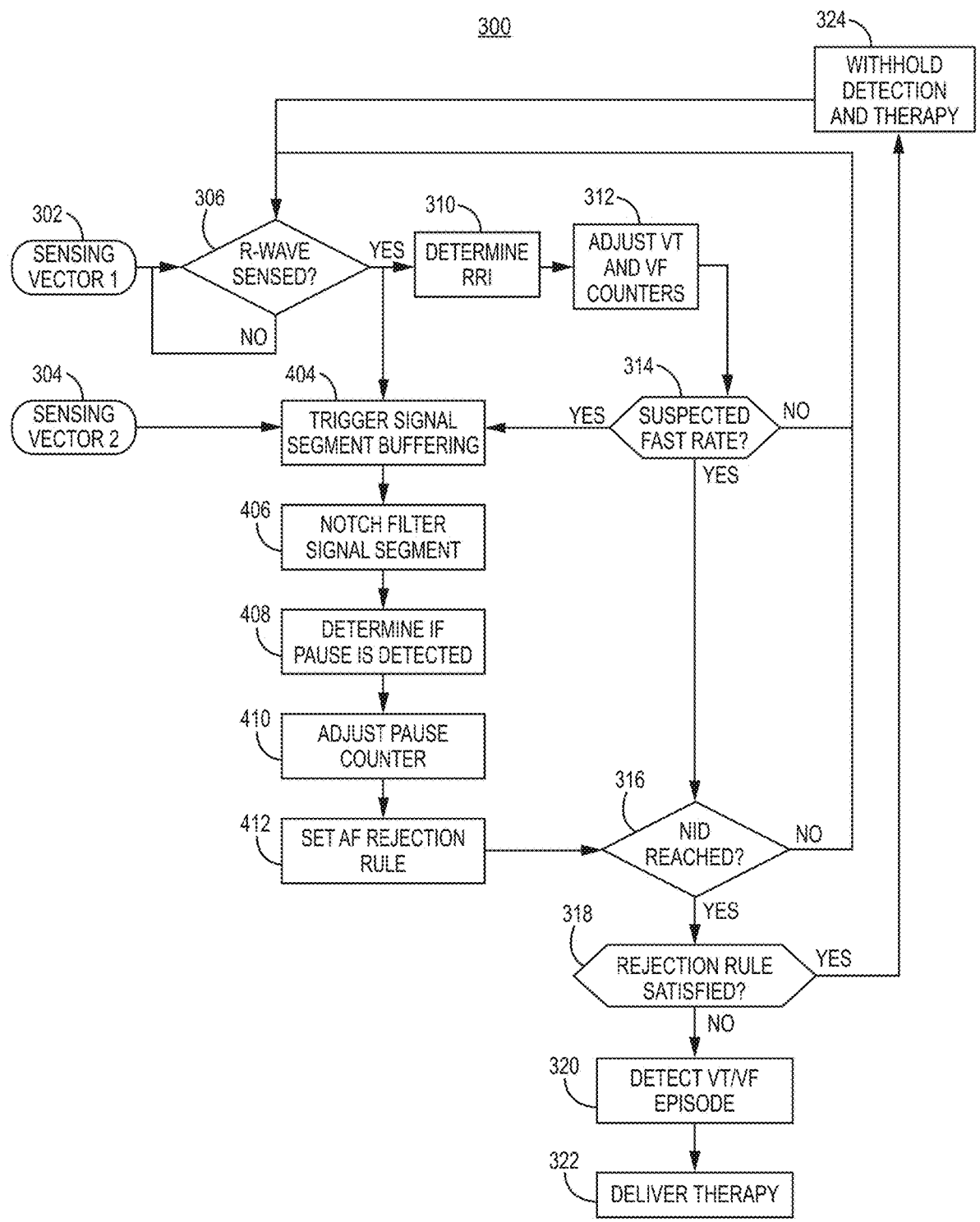
FIG. 7 is a flow chart of a method for detecting ventricular tachyarrhythmias according to one example using the rapidly conducted AF detection techniques disclosed herein.

FIG. 7 is a flow chart 300 of a method for detecting ventricular tachyarrhythmias according to one example using the rapidly conducted AF detection techniques disclosed herein. At block 302, a sensing electrode vector is selected by sensing circuit 86 for receiving a cardiac electrical signal by first sensing channel 83 used for sensing R-waves. The first sensing vector selected at block 302 for obtaining the cardiac electrical signal used for sensing R-waves may be a relatively short bipole, e.g., between electrodes 28 and 30 or between electrodes 28 and 24 of lead 16 or other electrode combinations as described above. The first sensing vector may be a vertical sensing vector (with respect to an upright or standing position of the patient) or approximately aligned with the cardiac axis for maximizing the amplitude of R-waves in the cardiac electrical signal for reliable R-wave sensing. In other examples, the first sensing vector may be a vector between one electrode carried along the distal portion 25 of lead 16 and the ICD housing 15 (shown in FIG. 1A). The sensing circuit 86 selects a second sensing vector at block 304 for receiving the cardiac signal that is buffered for obtaining cardiac signal segments for morphology analysis and SVT discrimination. As described above, in some instances, the second sensing vector is the same as the first sensing vector.

Sensing circuit 86 may produce an R-wave sensed event signal at block 306 in response to the first sensing channel 83 detecting the cardiac electrical signal crossing an R-wave sensing threshold outside of a blanking period. The R-wave sensed event signal may be passed to control circuit 80. In response to the R-wave sensed event signal, timing circuit 90 of control circuit 80 determines an RRI at block 310 ending with the current R-wave sensed event signal and beginning with the most recent preceding R-wave sensed event signal. The timing circuit 90 of control circuit 80 may pass the RRI timing information to the tachyarrhythmia detection circuit 92 which adjusts tachyarrhythmia interval counters, e.g., VT interval counter, VF interval counter and/or combined VT/VF interval counter, at block 312 as needed based on the RRI.

For example, if the RRI is shorter than the TDI and longer than the FDI, a VT interval counter is increased at block 312. The VT interval counter may be reset to zero if the RRI is longer than the TDI. If the RRI is shorter than the FDI, the VF counter is increased. A combined VT/VF interval counter may be increased if the RRI is less than the TDI. After updating the tachyarrhythmia interval counters at block 312, tachyarrhythmia detector 92 compares the VT and VF interval counter values to a suspected fast rate threshold at block 314. The suspected fast rate threshold is less than number of TDIs and FDIs required to detect VT and VF, i.e., less than the respective VT NID and VF NID. If a threshold number of short RRIs are counted, a fast ventricular rate is suspected but several more TDIs or FDIs are required before a VT or VF detection can be made. As described above, the fast rate threshold may be a count of two on the VT interval counter and a count of three on the VF interval counter in one example.

If a VT or VF detection interval counter has reached a fast rate threshold, "yes" branch of block 314, control circuit 80 enables cardiac signal segment buffering at block 404. In this example, the determination of parameters for detecting a pause in the suspected fast ventricular rate evidencing a rapidly conducted AF rhythm may be performed on an event-by-event basis only after at least one of the VT or VF interval counter values (or a combined VT/VF interval counter) has reached the suspected fast rate threshold.

If the suspected fast rate threshold is not reached by any of the tachyarrhythmia interval counters at block 314, the control circuit 80 returns to block 306 and waits for the next R-wave sensed event signal. Analysis of cardiac signal segments from the second cardiac electrical signal need not be performed for discriminating between SVT and VT/VF until at least a threshold number of VT or VF intervals is counted in anticipation of an NID being reached. In this way, control circuit 80 makes a determination of whether a pause is detected as evidence of a conducted AF rhythm only when a fast ventricular rate is suspected to conserve processing power requirements. Control circuit 80 may start analyzing pause detection parameters when the suspected fast rate threshold is reached, before the NID is reached, so that the detection of a pause indicative of a conducted AF rhythm can be made by the time the NID is reached. The VT or VF detection may be withheld based on pause detection, or the VT or VF detection is made without delay in the absence of pause detection.

As long as the suspected fast rate threshold is satisfied at block 314, control circuit 80 enables buffering of cardiac signal segments from the second cardiac electrical signal at block 404. In response to each R-wave sensed event signal produced by the first sensing channel 83 at block 306, control circuit 80 buffers the cardiac electrical signal received by the second sensing channel 85 over a predetermined time interval or number of sample points for a given sampling rate.

As illustrated in FIG. 6, a digitized segment of the cardiac electrical signal received by the second sensing channel 85 may be buffered over a time segment defined relative to the sample point time of the R-wave sensed event signal received from the first sensing channel 83. The digitized segment may be 100 to 500 ms long, for instance. In one example, the buffered segment of the second cardiac electrical signal is at least 48 sample points obtained at a sampling rate of 256 Hz, or approximately 188 ms, of which 24 sample points may precede and include the sample point at which the R-wave sensed event signal was received and 24 sample points may extend after the sample point at which the R-wave sensed event signal was received. In other examples, the cardiac electrical signal segment may be buffered at block 404 over a longer time interval for use in other cardiac signal analyses performed to detect noise in the cardiac signal, T-wave oversensing, or other sensing issues that may lead to a false VT or VF detection.

The buffered cardiac signal segment may be notch filtered at block 406. The notch filter applied at block 406 may correspond to the filter described in provisional U.S. Patent Pub. No. 2018/0028087, incorporated herein by reference in its entirety. The notch filtering performed at block 406 significantly attenuates 50-60 Hz electrical noise, muscle noise, other EMI, and other noise/artifacts in the stored cardiac signal segment from the second cardiac electrical signal.

In one example, notch filtering performed at block 406 is implemented in firmware as a digital integer filter. The output of the digital notch filter may be determined by firmware implemented in the second sensing channel 85 according to the equation $Y(n)=(x(n)+2*x(n-2)+x(n-4))/4$, where $x(n)$ is the amplitude of the nth sample point of the digital signal received by the notch filter 76 (FIG. 4), $x(n-2)$ is the amplitude of the n−2 sample point, and $x(n-4)$ is the amplitude of the n−4 sample point for a sampling rate of 256 Hz. $Y(n)$ is the amplitude of the nth sample point of the notch-filtered, digital second cardiac electrical signal. At a frequency of 60 Hz, the attenuation of the magnitude of $Y(n)$ is about −40 decibels (dB). At a frequency of 50 Hz, the attenuation is about −20 dB, and at 23 Hz, which may be typical of an R-wave of the cardiac electrical signal, the attenuation is limited to about −3 dB. Notch filtering at block 406 may therefore provide highly attenuated 50 and 60 Hz noise, muscle noise, other EMI, and other electrical noise/ artifacts while passing lower frequency cardiac signals, e.g., R-waves, in the cardiac electrical signal output of second sensing channel 85.

The sample point numbers indicated in the equation above for determining a notch-filtered signal may be modified as needed when a different sampling rate other than 256 Hz is used, and the resulting frequency response may differ somewhat from the example given above. In other examples, other digital filters may be used for attenuation of 50 and 60 Hz. For example, for a sampling rate of 256 Hz, a filtered signal Y(n) may be determined as Y(n)=(x(n)+x(n−1)+x(n−2)+x(n−3))/4 which may have relatively less attenuation at 50 and 60 Hz but acts as a low-pass, notch filter with relatively greater attenuation at higher frequencies (greater than 60 Hz).

Under the control of control circuit 80, a predetermined number of cardiac signal segments may be stored in memory 82 in a rolling, first-in-first-out buffer. For example, eight cardiac signal segments may be buffered in memory 82 in a first-in-first-out manner as long as the suspected fast rate is being detected based on a threshold VT or VF interval counter value. At block 408, control circuit 80 may determine if a pause is detected using the techniques described above in conjunction with FIGS. 5 and 6. For example, in response to the RRI ending with the currently sensed R-wave being greater than the pause threshold interval, the absolute difference between the peak amplitudes of the starting and trailing R-waves of the current RRI are compared to a difference threshold, which is half of the trailing R-wave peak amplitude in one example. The R-wave amplitudes may be determined from the first cardiac signal received by the first sensing channel 83 or the second cardiac signal received by the second sensing channel 85. In response to the R-wave amplitude difference being less than the difference threshold, control circuit 80 may determine a morphology match score for each of starting and trailing R-waves from the buffered, notch-filtered second cardiac electrical signal segments at block 408. The morphology match scores are compared to a match threshold, which may be adjusted from a higher match threshold value required for detecting SVT beats on a beat by beat basis as described above. A pause is detected by control circuit 80 at block 407 in response to the current RRI being greater than the pause threshold interval, both of the starting and trailing R-waves of the current RRI matching the SVT morphology template with a score greater than the adjusted match threshold, and the absolute difference between the peak amplitudes of the starting and trailing R-waves of the current RRI being less than the difference threshold.

In response to detecting a pause, control circuit 80 may adjust a pause counter or set a pause detection flag at block 410. In some examples, only one pause detection within the most recent twenty sensed R-waves is evidence of a rapidly conducted AF rhythm. In other examples, criteria for detecting a conducted AF rhythm may require one or more pauses detected within a predetermined number of the most recently sensed R-waves, which may be greater than or less than twenty sensed R-waves.

At block 412, control circuit 80 sets the status of an AF rejection rule based on the pause counter or flag value. The AF rejection rule status may be satisfied based on a count of detected pauses, e.g., based on N pauses detected out of the most recent M sensed R-waves. In some examples additional requirements must be satisfied in order for the AF rejection rule to be satisfied. For example, in order to reject a VT or VF detection based on pause detection(s) as evidence of a conducted AF rhythm, the median RRI (determined over the most recent 8 or other selected number of RRIs) may be required to be greater than the SVT limit in order to set the AF rejection rule as being satisfied. Additionally or alternatively, the VF interval counter may be required to be greater than a rapidly conducted AF threshold count. The VF interval counter may be required to have reached a count of at least 6, for example, in order to set the AF rejection rule as being satisfied at block 412.

If the criteria for detecting a conducted AF rhythm are satisfied, control circuit 80 sets the AF rejection rule at block 412 to indicate that evidence of a conducted AF rhythm is detected. As an example if at least one pause has been detected out of the most recent twenty sensed R-waves, the VF interval count value is greater than or equal to six, and the median RRI (e.g., determined from the most recent eight RRIs) is greater than the programmed SVT limit, control circuit 80 may set the AF rejection rule to "true" by setting a flag or digital value stored in memory 82 to a high value. If the conducted AF rhythm criteria are not satisfied, e.g., less than N pauses detected out of the most recent M sensed R-waves, the median RRI is less than the SVT limit, and/or the VF interval count has not yet reached a rapidly conducted AF threshold count, the AF rejection rule may be set to "false," e.g., by setting the flag or digital value stored in memory 82 to zero or a digital low value. The status of the AF rejection rule may be adjusted at block 412 on a beat by beat basis as needed based on updates to the pause detection counter (block 410) and other rapidly conducted AF rhythm criteria as long as the suspected fast rate criteria are satisfied (at block 314).

If an NID is not yet reached by one of the VT, VF or combined VT/VF interval counters at block 316, control circuit 80 returns to block 306 to sense the next R-wave, determine the next RRI for updating the interval counters, and buffer the next segment of the second cardiac signal if the suspected fast rate criteria are still satisfied at block 314. The AF rejection rule status may be updated at block 412 based on the analysis of the next RRI and associated R-wave amplitudes and morphology match scores.

If an NID is reached at block 316 by one of the VT, VF or combined VT/VF interval counters, control circuit 80 checks if a rejection rule is satisfied or set to "true" at block 318. If the AF rejection rule is set to "true," VT or VF detection is withheld at block 324 even though the NID has been reached. No VT or VF therapy is delivered by therapy delivery circuit 84. Control circuit 80 advances to the next sensed R-wave to continue updating the VT and VF interval counters and analyzing the next RRI and the associated R-wave amplitudes and morphology match scores if the RRI is greater than the pause threshold interval to update the status of the AF rejection rule at block 412.

If the VT or VF NID is reached at block 316 and the AF rejection rule is set to "false" ("no" branch of block 318), the VT or VF episode may be detected at block 320. The AF rejection rule may be one of multiple VT/VF rejection rules that may be set by control circuit 80. Other examples of rejection rules that may be set based at least in part on an analysis of the second cardiac electrical signal after the suspected fast rate criteria are satisfied are described in the above incorporated patent applications and may include a T-wave oversensing rejection rule, an SVT beat morphology rejection rule, a gross morphology rejection rule, a noise rejection rule, as examples. Control circuit 80 detects VT or VF at block 320 in response to the respective NID being reached without a rejection rule being satisfied. For instance, if at least the AF rejection rule is set to "false," a VT or VF episode may be detected at block 320 in response to the NID being reached. Control circuit 80 controls therapy delivery circuit 84 to deliver a therapy at block 322, which may include one or more of ATP, a CV/DF shock, and/or post-shock pacing pulses in some examples.

Thus, techniques for withholding a VT or VF detection based on detecting at least one pause indicating a high likelihood of a rapidly conducted AF rhythm are presented herein. It should be understood that, depending on the example, certain acts or events of any of the methods described herein can be performed in a different sequence, may be added, merged, or left out altogether (e.g., not all described acts or events are necessary for the practice of the method). Moreover, in certain examples, acts or events may be performed concurrently, e.g., through multi-threaded processing, interrupt processing, or multiple processors, rather than sequentially. In addition, while certain aspects of this disclosure are described as being performed by a single circuit or unit for purposes of clarity, it should be understood that the techniques of this disclosure may be performed by a combination of units or circuits associated with, for example, a medical device.

In one or more examples, the functions described may be implemented in hardware, software, firmware, or any combination thereof. If implemented in software, the functions may be stored as one or more instructions or code on a non-transitory computer-readable medium and executed by a hardware-based processing unit. Computer-readable media may include computer-readable storage media, which corresponds to a tangible, non-transitory medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. Also, the techniques could be fully implemented in one or more circuits or logic elements.

Thus, techniques have been presented in the foregoing description with reference to specific examples. It is to be understood that various aspects disclosed herein may be combined in different combinations than the specific combinations presented in the accompanying drawings. It is appreciated that various modifications to the referenced examples may be made without departing from the scope of the disclosure and the following claims.

What is claimed is:

1. A medical device comprising:
a sensing circuit configured to:
receive one or more cardiac electrical signals; and
sense ventricular event signals from the one or more cardiac electrical signals;
a memory storing a morphology template and a match threshold;
a control circuit coupled to the sensing circuit and configured to:
determine a first morphology matching score between the morphology template and a first ventricular event signal of the one or more cardiac electrical signals sensed by the sensing circuit;
determine a second morphology matching score between the morphology template and a second ventricular event signal of the one or more cardiac electrical signals, the second ventricular event signal sensed consecutively with the first ventricular event signal;
determine if the first morphology match score and the second morphology match score each meet the match threshold;
determine from a plurality of ventricular event signals sensed by the sensing circuit that a threshold number of tachyarrhythmia intervals to detect a ventricular tachyarrhythmia is met;
in response to determining that at least the first morphology match score and the second morphology match score each meet the match threshold, do not detect a ventricular tachyarrhythmia based on the threshold number of tachyarrhythmia intervals to detect the ventricular tachyarrhythmia being met; and
in response to determining that at least one of the first morphology match score and the second morphology match score does not meet the match threshold, detect the ventricular tachyarrhythmia based on at least the threshold number of tachyarrhythmia intervals to detect the ventricular tachyarrhythmia being met; and
a therapy delivery circuit configured to deliver a therapy in response to the control circuit detecting the ventricular tachyarrhythmia.

2. The medical device of claim 1 wherein the control circuit is further configured to:
determine a first feature of the one or more cardiac electrical signals, the first feature corresponding to the first ventricular event signal;
determine a second feature of the one or more cardiac electrical signals, the second feature corresponding to the second ventricular event signal; and
determine if a difference between the first feature and the second feature is less than a difference threshold;
not detect the ventricular tachyarrhythmia, based on the threshold number of tachyarrhythmia intervals to detect the ventricular tachyarrhythmia being met, in response to at least determining that the difference between the first feature and the second feature is less than the difference threshold and that the first morphology match score and the second morphology match score each meet the match threshold; and
detect the ventricular tachyarrhythmia based on at least the threshold number of tachyarrhythmia intervals to detect the ventricular tachyarrhythmia being met when at least one of:
the difference between the first feature and the second feature is not less than the difference threshold;
the first morphology match score does not meet the match threshold; or
the second morphology match score does not meet the match threshold.

3. The medical device of claim 2 wherein the control circuit is further configured to:
determine the first feature as a first amplitude corresponding to the first ventricular event signal; and
determine the second feature as a second amplitude corresponding to the second ventricular event signal.

4. The medical device of claim 2 wherein the control circuit is further configured to determine the difference threshold based on one of the first feature or the second feature.

5. The medical device of claim 1, wherein:
the memory is further configured to store a supraventricular tachycardia beat detection match threshold; and
the control circuit is further configured to determine the match threshold based on the supraventricular tachycardia beat detection match threshold.

6. The medical device of claim 5 wherein the control circuit is further configured to:
select a percentage that is scaled to the supraventricular tachycardia beat detection match threshold;
determine the match threshold based on the supraventricular tachycardia beat detection match threshold by determining the scaled percentage of the supraventricular tachycardia beat detection match threshold.

7. The medical device of claim 1 wherein the control circuit is further configured to:
detect a sinus rhythm from the at least one cardiac electrical signal;
establish, from a first cardiac electrical signal of the one or more cardiac electrical signals, the morphology template representative of an R-wave morphology of the first cardiac electrical signal during the sinus rhythm.

8. The medical device of claim 1 wherein the control circuit is further configured to:
determine that the first ventricular event signal and the second ventricular event signal define a first RR interval that is evidence of a supraventricular tachyarrhythmia when at least the first morphology match score and the second morphology match score each meet the match threshold;
detect, from the one or more cardiac electrical signals, a plurality of RR intervals that are evidence of supraventricular tachyarrhythmia; and
in response to detecting the plurality of RR intervals that are evidence of supraventricular tachyarrhythmia, do not detect the ventricular tachyarrhythmia based on the threshold number of tachyarrhythmia intervals to detect the ventricular tachyarrhythmia being met.

9. The medical device of claim 1 wherein:
the sensing circuit is further configured to:
sense a leading R-wave from a first cardiac electrical signal of the one or more cardiac electrical signals, the leading R-wave corresponding to the first ventricular event signal;
sense a trailing R-wave from the first cardiac electrical signal, the trailing R-wave corresponding to the second ventricular event signal; and
sense a second cardiac electrical signal of the one or more cardiac electrical signals; and
the control circuit is further configured to determine the first morphology matching score and the second morphology matching score from the second cardiac electrical signal.

10. The medical device of claim 1 wherein the control circuit is further configured to:
determine an RR interval from the first ventricular event signal to the second ventricular event signal;
determine if the RR interval is greater than a threshold interval; and
do not detect the ventricular tachyarrhythmia based on the threshold number of tachyarrhythmia intervals to detect the ventricular tachyarrhythmia being met when at least the first morphology match score and the second morphology match score each meet the match threshold and the RR interval is greater than the threshold interval.

11. A method comprising:
receiving one or more cardiac electrical signals;
sensing ventricular event signals from the one or more cardiac electrical signals;
storing a morphology template and a match threshold;
determining a first morphology matching score between the morphology template and a first ventricular event signal of the one or more cardiac electrical signals sensed by the sensing circuit;
determining a second morphology matching score between the morphology template and a second ventricular event signal of the one or more cardiac electrical signals, the second ventricular event signal sensed consecutively with the first ventricular event signal;
determining if the first morphology match score and the second morphology match score each meet the match threshold;
determining from a plurality of ventricular event signals that a threshold number of tachyarrhythmia intervals to detect a ventricular tachyarrhythmia is met;
in response to determining that at least the first morphology match score and the second morphology match score each meet the match threshold, not detecting a ventricular tachyarrhythmia based on the threshold number of tachyarrhythmia intervals to detect the ventricular tachyarrhythmia being met; and
in response to determining that at least one of the first morphology match score and the second morphology match score does not meet the match threshold, detecting the ventricular tachyarrhythmia based on at least the threshold number of tachyarrhythmia intervals to detect the ventricular tachyarrhythmia being met; and
delivering a therapy in response to detecting the ventricular tachyarrhythmia.

12. The method of claim 11 further comprising:
determining a first feature of the one or more cardiac electrical signals, the first feature corresponding to the first ventricular event signal;
determining a second feature of the one or more cardiac electrical signals, the second feature corresponding to the second ventricular event signal; and
determining if a difference between the first feature and the second feature is less than a difference threshold;
not detecting the ventricular tachyarrhythmia, based on the threshold number of tachyarrhythmia intervals to detect the ventricular tachyarrhythmia being met, in response to at least determining that the difference between the first feature and the second feature is less than the difference threshold and that the first morphology match score and the second morphology match score each meet the match threshold; and
detecting the ventricular tachyarrhythmia based on at least the threshold number of tachyarrhythmia intervals to detect the ventricular tachyarrhythmia being met when at least one of:
the difference between the first feature and the second feature is not less than the difference threshold;
the first morphology match score does not meet the match threshold; or
the second morphology match score does not meet the match threshold.

13. The method of claim 12 further comprising:
determining the first feature as a first amplitude corresponding to the first ventricular event signal; and
determining the second feature as a second amplitude corresponding to the second ventricular event signal.

14. The method of claim 12 wherein the control circuit is further configured to determine the difference threshold based on one of the first feature or the second feature.

15. The method of claim 11, further comprising:
storing a supraventricular tachycardia beat detection match threshold; and
determining the match threshold based on the supraventricular tachycardia beat detection match threshold.

16. The method of claim 15 further comprising:
selecting a percentage that is scaled to the supraventricular tachycardia beat detection match threshold; and
determining the match threshold based on the supraventricular tachycardia beat detection match threshold by determining the scaled percentage of the supraventricular tachycardia beat detection match threshold.

17. The method of claim 11 further comprising:
detecting a sinus rhythm from the at least one cardiac electrical signal;
establishing, from a first cardiac electrical signal of the one or more cardiac electrical signals, the morphology template representative of an R-wave morphology of the first cardiac electrical signal during the sinus rhythm.

18. The method of claim 11 further comprising:
determining that the first ventricular event signal and the second ventricular event signal define a first RR interval that is evidence of a supraventricular tachyarrhythmia when at least the first morphology match score and the second morphology match score each meet the match threshold;
detecting, from the one or more cardiac electrical signals, a plurality of RR intervals that are evidence of supraventricular tachyarrhythmia; and
in response to detecting the plurality of RR intervals that are evidence of supraventricular tachyarrhythmia, do not detect the ventricular tachyarrhythmia based on the threshold number of tachyarrhythmia intervals to detect the ventricular tachyarrhythmia being met.

19. The method of claim 11 further comprising:
sensing a leading R-wave from a first cardiac electrical signal of the one or more cardiac electrical signals, the leading R-wave corresponding to the first ventricular event signal;
sensing a trailing R-wave from the first cardiac electrical signal, the trailing R-wave corresponding to the second ventricular event signal; and
sensing a second cardiac electrical signal of the one or more cardiac electrical signals; and
determining the first morphology matching score and the second morphology matching score from the second cardiac electrical signal.

20. The method of claim 11 further comprising:
determining an RR interval from the first ventricular event signal to the second ventricular event signal;
determining if the RR interval is greater than a threshold interval; and
not detecting the ventricular tachyarrhythmia based on the threshold number of tachyarrhythmia intervals to detect the ventricular tachyarrhythmia being met when at least the first morphology match score and the second morphology match score each meet the match threshold and the RR interval is greater than the threshold interval.

21. A non-transitory computer readable medium storing a set of instructions that, when executed by a control circuit of a medical device, cause the medical device to:
receive one or more cardiac electrical signals;
sense ventricular event signals from the one or more cardiac electrical signals;
determine a first morphology matching score between the morphology template and a first ventricular event signal of the one or more cardiac electrical signals sensed by the sensing circuit;
determine a second morphology matching score between the morphology template and a second ventricular event signal of the one or more cardiac electrical signals, the second ventricular event signal sensed consecutively with the first ventricular event signal;
determine if the first morphology match score and the second morphology match score each meet the match threshold;
determine from a plurality of ventricular event signals that a threshold number of tachyarrhythmia intervals to detect a ventricular tachyarrhythmia is met;
in response to determining that at least the first morphology match score and the second morphology match score each meet the match threshold, do not detect a ventricular tachyarrhythmia based on the threshold number of tachyarrhythmia intervals to detect the ventricular tachyarrhythmia being met; and
in response to determining that at least one of the first morphology match score and the second morphology match score does not meet the match threshold, detect the ventricular tachyarrhythmia based on at least the threshold number of tachyarrhythmia intervals to detect the ventricular tachyarrhythmia being met; and
deliver a therapy in response to detecting the ventricular tachyarrhythmia.

* * * * *